United States Patent
Barnard et al.

(10) Patent No.: US 6,294,390 B1
(45) Date of Patent: Sep. 25, 2001

(54) COVALENTLY IMMOBILIZED FLUOROIONOPHORES FOR OPTICAL ION SENSORS

(75) Inventors: Steven Mark Barnard, San Diego, CA (US); René Beerli, Basel; Joseph Berger, Muttenz, both of (CH); David Reinhoudt, Hengelo (NL); Adrian Waldner, Allschwil (CH)

(73) Assignee: Novartis Ag, Basel (CH)

( * ) Notice: Subject to any disclaimer, the term of this patent is extended or adjusted under 35 U.S.C. 154(b) by 0 days.

(21) Appl. No.: 09/230,217

(22) PCT Filed: Jul. 21, 1997

(86) PCT No.: PCT/EP97/03913

§ 371 Date: Jan. 21, 1999

§ 102(e) Date: Jan. 21, 1999

(87) PCT Pub. No.: WO98/03497

PCT Pub. Date: Jan. 29, 1998

(30) Foreign Application Priority Data

Jul. 22, 1996 (CH) .................................................. 1832-96

(51) Int. Cl.[7] .......................... G01N 21/76; G01N 21/75; C07D 487/22
(52) U.S. Cl. .......................... 436/172; 436/164; 436/800; 549/346; 549/347
(58) Field of Search ................................ 436/73, 79, 172, 436/164, 800; 549/346, 347

(56) References Cited

U.S. PATENT DOCUMENTS

| 4,367,072 | 1/1983 | Vögtle et al. ........................ 436/501 |
| 5,177,221 | * 1/1993 | Cram et al. ........................... 549/348 |

FOREIGN PATENT DOCUMENTS

| 0623599A1 | 11/1994 | (EP) . |
| 1452777 | 9/1966 | (FR) . |
| 8900997 | 2/1989 | (WO) . |
| 9312428 | 6/1993 | (WO) . |

OTHER PUBLICATIONS

Journal of the American Chemical Society. Ionoresistivity as a Highly Sensitive Sensory Probe: Investigations of Polythiophenes Functionalized with Calix[4]arene–Based Ion Receptors. Marsella et al. May, 1995.*
American Chemical Society, Polymer Chemistry Division. A Conjugated Polymer Based Na+ Sensor: Thershold Behavior due to Energy Migration. Goldfinger et al. May, 1995.*
Shortreed et al., "Fluorescent Fiber–Optic Calcium Sensor for Physiological Measurements," Anal. Chem., vol. 68, 1996, pp. 1414–1418.
Perez–Jimenez et al., "New Fluoroionophores for Alkali––metal Cations based Tetrameric Calixarenes, " J. Mater. Chem., vol. 4(1), 1994, pp. 145–151.

* cited by examiner

Primary Examiner—Jill Warden
Assistant Examiner—LaToya I. Cross
(74) Attorney, Agent, or Firm—Wenderoth, Lind & Ponack, L.L.P.

(57) ABSTRACT

Compounds, constructed in modular manner, of formula (I), $$I-R_{01}-T(-R_{03}-G)-R_{02}-F,$$ (I)

wherein
 I is the monovalent residue of an ionophore,
 F is the monovalent residue of a fluorophore,
 G is a functional group,
 T is a trivalent organic radical and
 $R_{01}$, $R_{02}$ and $R_{03}$ are each independently of the others a direct bond or a bridging group.

The compounds may be used in immobilized form as active components in polymer membranes of optical sensors for the detection of ions. The sensors are distinguished by a long usable life and a high degree of sensitivity.

26 Claims, No Drawings

COVALENTLY IMMOBILIZED FLUOROIONOPHORES FOR OPTICAL ION SENSORS

This application is a 371 of PCT/EP97/03913 filed Jul. 21, 1997.

The present invention relates to monomeric fluoroionophores that comprise a fluorophore, an ionophore and a functional group covalently bound either directly or via a bridging group to a trivalent organic radical; to homo- and co-polymers of those monomeric fluoroionophores; to processes for the preparation of the monomeric fluoroionophores and polymers thereof; to a coating composition comprising a solvent and a homo- or co-polymer of the monomeric fluoroionophores; to a coated material comprising a support and a layer of the homo- or co-polymers of the monomeric fluoroionophores; to a sensor for the determination of ions, polar substances or lipophilic substances especially in aqueous solutions that comprise the immobilised fluoroionophores in the active layer; to a fluorescence-optical method for the qualitative or quantitative determination of ions, polar substances or lipophilic substances especially in aqueous solutions using the sensor; and to the use of the homo- or co-polymers of those monomeric fluoroionophores as the active layer in fluorescence-optical sensors.

The optical determination of ions has recently gained greater importance, the presence or concentration of ions being measured, for example, by means of a change in the absorption or fluorescence of a suitable dye. The sensors, also called optrodes, generally consist of a transparent support material and an active layer. The active layer normally comprises a transparent hydrophobic polymer and a lipophilic plasticiser for the purpose of obtaining adequate diffusion of the ions and adequate solubility of the active components. Active components are a specific ionophore as a complexing agent for ions, a counter-ion for maintaining electrical neutrality, and an indicator substance which, as a result of a chemical change or a physical change in the environment, emits a measurable optical signal. The disadvantages of many such optical sensors are, for example, that their response times are too long, they are not sufficiently stable, they are pH-dependent, and the active constituents are washed out, so that their useful life is too short or they have to be recalibrated during use.

The response times may be shortened by covalent linkage of ionophore and fluorophore to form the so-called fluoroionophores. Such fluoroionophores are known from WO 89/00997 and U.S. Pat. N. 4,367,072. Even with the use of those fluoroionophores, however, the problem of washing out cannot be fully overcome.

In *J. Mater. Chem.* 4(1), (1994), pp. 145–151, Perez-Jimenez et al. describe two novel fluoroionophores that comprise four anthracene units covalently bound to calix[4] arene via an amide or ester bond. Disadvantageous fluorescence-quenching effects may occur as a result of the close adjacency of the four anthracene units in the molecule.

Shortreed et al. describe in *Anal. Chem.* (1996), 68, p. 1414–1418 a calcium-sensitive fluoroionophore that contains a vinyl group bound to the ionophore and that is immobilised at the distal end of an optical fibre by photopolymerisation in acrylamide. Washing out is prevented by that method. The ionophores must, however, contain two functional groups to construct the monomers, which substantially limits the possible choices, since the ion affinity can be substantially reduced by such structural changes.

It has now been found that monofunctionalised ionophores and fluorophores can be covalently bound either directly or via a bridging group to a trifunctional group, which can then be polymerised or bonded to an inorganic or organic material. The immobilised materials are, surprisingly, still suitable for fluorescence detection of ions because the complexing of ions by way of interactions between fluorophore and ionophore still results in a measurable change in fluorescence, and consequently a measurement that is substantially independent of pH is possible. As a result, a direct analysis of ions in body fluids (for example blood, urine, serum), natural waters, waste water or liquid mixtures from chemical reaction processes is possible in which disadvantages, such as washing out of the active components of a sensor, are avoided and, surprisingly, long useful lives and also a high degree of accuracy of measurement are achieved, even with repeated use.

This idea in addition embraces a modular construction of the building blocks (fluorophore, ionophore and functional group) that are to be covalently bound to a trivalent radical, representing a great simplification in synthesis and rendering possible a high degree of flexibility and range of variation resulting from the possibility of interchanging the individual building blocks. In addition, optimisation to the particular intended purpose is possible by means of the choice of building blocks, the nature and length of the bridging groups and the nature of the base materials used for the immobilisation.

The invention relates firstly to compounds of formula (I),

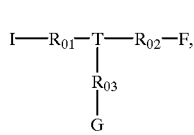

(I)

wherein
I is the monovalent residue of an ionophore,
F is the monovalent residue of a fluorophore,
G is a functional group,
T is a trivalent organic radical and
$R_{01}$, $R_{02}$ and $R_{03}$ are each independently of the others a direct bond or a bridging group.

Preferably, $R_{01}$, $R_{02}$ and $R_3$ are each independently of the others a bridging group.

The ionophores may be natural or synthetic organic compounds that contain a plurality of mostly alternating electron-rich hetero atoms, such as, for example, S, N and especially O, in an open-chained or cyclic carbon chain, and that enable the ions to be measured to be complexed selectively. Such ionophores are described, for example, in U.S. Pat. No. 4,645,744.

The monovalent ionophores from which I in formula (I) is derived may be substances that have an oligoether, polyether, oligoester, polyester, oligoamide or polyamide structure. Examples of such suitable substances may be crown ethers, coronandenes, cryptandenes, calixarenes, podandene or derivatives thereof, also cyclic peptides, for example valinomycin or nonactin, peptides such as gramicidin, and peptides that in the presence of the ion to be determined change their secondary, tertiary or quaternary structure for bonding the ion. It is also possible to use tetrahydrofuran-containing macrolides bonded via ester bridges, and analogous substances that are able to regulate transport in biological systems, or cyclic oligosaccharides, such as, for example, cyclodextrins or cyclophanes.

The functional group G may be carboxy or sulfonic acid, carboxy or sulfonic acid halide, carboxy or sulfonic acid amide, carboxy or sulfonic acid ester, thiol, amine, hydroxyl, cyanate, isocyanate, oxime, aldehyde or ketone groups, or polymerisable groups, such as, for example, olefinically unsaturated groups. Halide denotes preferably chloride or bromide.

The functional group G is preferably a hydroxyl, thiol, isocyanate, carboxyl, carboxamide, carboxyhalide, carboxyalkoxy or amine group.

The functional group G may also be a polymerisable group and in that case is preferably a vinyl group that is unsubstituted or substituted by $C_1$–$C_4$alkyl. Further examples of polymerisable groups are: diol, diamine, diisocyanate, dicarboxylic acid, dicarboxylic acid dihalide, dicarboxylic acid diamide and dicarboxylic acid diester groups.

The polymerisable group is bonded to the trivalent radical T preferably via the bridging group $R_{O3}$. The polymerisable radical may be selected from the group —O—$R_8$, —S—$R_8$, —$NR_7R_8$, —$NR_7C(O)R_8$, —$OC(O)R_8$, —$C(O)OR_8$, —$C(O)R_8$, —$C(O)NR_7R_8$, —CH=N—O—$R_8$ and —NH—C(O)—$NR_7R_8$, wherein $R_7$ is H or $C_1$–$C_4$alkyl and $R_8$ is an olefinic group having from 1 to 12 carbon atoms, preferably from 1 to 4 carbon atoms, it being possible for those groups to be bonded to the trivalent radical T directly or via a bridging group $R_{O3}$, for example $C_1$–$C_{20}$alkylene. Those radicals are preferably —$NR_7C(O)R_8$ wherein $R_7$ is H and $R_8$ is an olefinic group having preferably from 2 to 20, especially from 2 to 12, and more especially from 2 to 6, carbon atoms.

$R_8$ is preferably an ethylenically unsaturated organic group of formula (V)

—$CR_9$=$CHR_{10}$,                                (V), wherein $R_9$ is H or $C_1$–$C_4$alkyl, especially methyl; and $R_{10}$ is H, $C_1$–$C_{12}$alkyl, phenyl or benzyl.

$R_9$ is preferably H or methyl and $R_{10}$ is preferably H.

The polymerisable group may be derived, for example, from ethylenically unsaturated monocarboxylic acids, alcohols, amines or isocyanates, such as, for example, allyl alcohol, allylamine, allyl isocyanate, crotonyl alcohol; acrylic or methacrylic acid.

The trivalent radical T in formula I may be open-chained or cyclic and contains preferably at least 1, especially at least 2, and more especially at least 3 carbon atoms. It may contain up to 30, preferably up to 20, especially up to 16 and more especially up to 12, atoms selected from the group C, O, S and N. The radical T may be substituted, for example by $C_1$–$C_4$alkyl or $C_1$–$C_4$alkoxy.

The trivalent radical may be, for example, $C_1$–$C_{20}$-, especially $C_2$–$C_{12}$-, and more especially $C_2$–$C_6$-alkanetriyl, which may be linear or branched and may be interrupted by one or more, preferably from 1 to 3, hetero atoms selected from the group O, S and N. Examples include methanetriyl, 1,1,1-ethanetriyl, 1,1,2-ethanetriyl, 1,2,3-, 1,1,2- and 1,1,3-propanetriyl, 1,2,3-, 1,2,4-, 2,2,3-, 2,2,4- and 1,1,4-butanetriyl, 1,2,3-, 1,2,4-, 1,2,5-, 2,3,4-, 2,3,5- and 1,1,5pentylene, 1,2,3-, 1,2,4-, 1,2,5-, 1,2,6-, 1,3,5-, 1,3,6-, 2,4,6-, 2,5,6- and 1,1,6-hexanetriyl, heptanetriyls, octanetriyls, nonanetriyls, decanetriyls, undecanetriyis, dodecanetriyls, tetradecanetriyls, hexadecanetriyls, octadecanetrnyis, —N[($CH_2$)—]$_2$, —N[($CH_2CH_2$)—]$_2$, N[($CH_2CH_2$)—]$_3$, HC[($CH_2CH_2$)—]$_3$ and $CH_3$CH[($CH_2CH_2$)—]$_3$.

The trivalent radical may be, for example, a trivalent cycloaliphatic radical having from 3 to 12, preferably from 3 to 8, especially from 4 to 7 and more especially 5 or 6, carbon atoms in the ring, or a heterocycloaliphatic radical having from 3 to 12, preferably from 3 to 8, especially from 4 to 7 and more especially 5 or 6, atoms in the ring and from 1 to 3, preferably 1 or 2, hetero atoms, especially 1 hetero atom, selected from the group O, S and N, preferably N. The heterocycloaliphatic radicals contain preferably at least 2 carbon atoms in the ring, especially from 2 to 11, more especially from 3 to 10, carbon atoms in the ring. Examples include cyclopropanetriyl, cyclobutanetriyl, cyclopentylene, 1,2,3-, 1,2,4-, 1,3,5- and 1,2,5-cyclohexanetriyl, 1,2,3-, 1,2, 4-, 1,3,5-, 1,2,5-, 1,2,6-, 1,3,6- and 1,4,7-cycloheptanetriyl, 1,2,3-, 1,2,4-, 1,3,5-, 1,2,5-, 1,2,6-, 1,3,6-, 1,4,6-, 1,2,7-, 1,2,8-, 1,3,8-, 1,4,8- and 1,4,7-cyclooctanetriyl, cyclononanetriyls, cyclodecanetriyls, cyclodecanetriyls, cyclododecanetriyls, aziridinetriyl, azetidinetriyl, 1,2,3-, 1,2,4-, 1,2,5-, 2,3,4- and 2,3,5-pyrrolidine, 1,3,4-$\Delta^3$-pyrrolinetriyl, 1,2,3-, 1,2,4-, 1,3,5-, 1,2,5- and 2,3,5-piperidinetriyl, and 2,3,4-tetrahydrofurantriyl. The trivalent cyclic radical may contain double bonds in the ring. It may also be linked to other cycloaliphatic rings (for example bicyclohexanetriyls or methylenebiscyclohexyltriyls) or fused to other cycloaliphatic rings (for example decalinetriyls, nobornanetriyls).

The trivalent radical may be, for example, a trivalent aromatic radical having from 6 to 18, preferably from 6 to 14, especially from 6 to 10 and more especially 6, carbon atoms in the ring, or a heteroaromatic radical having in the ring a total of from 5 to 17, preferably from 5 to 13, especially from 5 to 9, and more especially 5 or 6, atoms, and from 1 to 3, especially 1 or 2, hetero atoms, more especially 1 hetero atom, selected from the group O, S and N, preferably N. The heteroaromatic radicals contain especially at least 3 carbon atoms in the ring, more especially 4 or 5 carbon atoms in the ring. The trivalent aromatic radical may be a linked aromatic radical (for example biphenyltriyl or methylenebisphenyltriyl) or a fused aromatic radical (for example naphthalenetriyl). Examples include 1,2,3-, 1,2,4- and 1,3,5-benzenetriyl, 1,3,6-, 1,3,7-, 2,3,6- and 2,3,7-naphthalenetriyl, 2,3,4-, 2,3,5-, 2,3,6- and 2,4,6-pyridinetriyl, 1,2,3-, 1,2,4-, 1,2,5-, 1,3,5- and 1,3,4-pyrroletriyl, 2,3,4-, 2,3,5- and 2,4,5-thiophenetriyl, 2,3,4-, 2,3,5- and 2,4,5-furantriyl, 2,4,5-, 2,4,6- and 4,5,6-pyrimidinetriyl, 1,2,3-, 1,2,4-, 1,3,5-, 1,3,6- and 3,5,6-indoletriyl, 3,5,6-thionaphthenetriyl, 1,3,5- and 1,3,4-pyrazoletriyl, 1,2,4- and 1,2,5-imidazoletriyl, 3,6,7-quinolinetriyl, 1,6,7-isoquinolinetriyl, 2,3,5-pyrazinetriyl, 3,4,5-pyridazinetriyl and 2,8,9-purinetriyl.

The trivalent radical T in formula I may be a radical of formula Ib or Ic

=$T_1$—$R_{O4}$—                                (Ib),

—$T_2$—$R_{O5}$=                                (Ic), wherein $T_1$ is a cycloaliphatic, heterocycloaliphatic, aromatic or heteroaromatic trivalent radical, $T_2$ is a cycloaliphatic, heterocycloaliphatic, aromatic or heteroaromatic divalent radical, $R_{O4}$ is a divalent aliphatic radical having from 1 to 20 carbon atoms, and $R_{O5}$ is a trivalent aliphatic radical having from 1 to 20 carbon atoms.

The same definitions, preferences and illustrative embodiments as specified above for the trivalent radical T in formula I apply to $T_1$ and $T_2$ as cycloaliphatic, heterocycloaliphatic, aromatic or heteroaromatic radicals.

$R_{O4}$ and $R_{O5}$ as aliphatic radicals contain preferably from 2 to 12, especially from 2 to 8, and more especially from 2 to 4, carbon atoms. The aliphatic radicals may be linear or branched.

Examples of divalent radicals $R_{04}$ are methylene, ethylene, 1,2- and 1,3-propylene, 1,1- and 2,2-propylidene, 1,2-, 1,3- and 1,4-butylene, pentylenes, hexylenes, heptylenes, octylenes, decylenes, dodecylenes, tetradecylenes, hexadecylenes and octadecylenes.

Examples of trivalent radicals $R_{05}$ are methanetriyl, 1,2,2-ethanetriyl, 1,2,3- and 2,3,3-propanetriyl, 1,2,3-, 1,2,4-, 2,3,4- and 1,4,4-butanetriyl.

The position of the substituents I, F and G in the compounds of formula I is in itself optional. It is advantageous, however, for the substituents I and F to be close to one another when short bridging groups are present, in order to achieve adequate intramolecular interaction for the change in fluorescence. In that case 1,1-, 1,2- and 1,3-positions are preferred. The bridging groups in that case have chain lengths of, for example, from 2 to 10, especially from 2 to 6 and more especially from 2 to 4, atoms. If the bridging groups chosen are longer, the change in fluorescence may occur by way of an intermolecular interaction, and consequently in that case the positions may also be so selected that greater spacing is possible, for example 1,4-, 1,5- or 1,6-positions. The position of the functional group G, on the other hand, may be selected as desired. For reasons associated with synthesis, positions more remote from the groups I and F are preferred, for example a 4-, 5- or 6-position based on a 1,1- or 1,2-position of I and F. The spacing may alternatively or additionally be controlled by way of the chain length of the bridging group.

The trivalent radical T may be, for example, a trivalent radical derived from a compound of one of the following formulae (the three functional groups are indicated in each case):

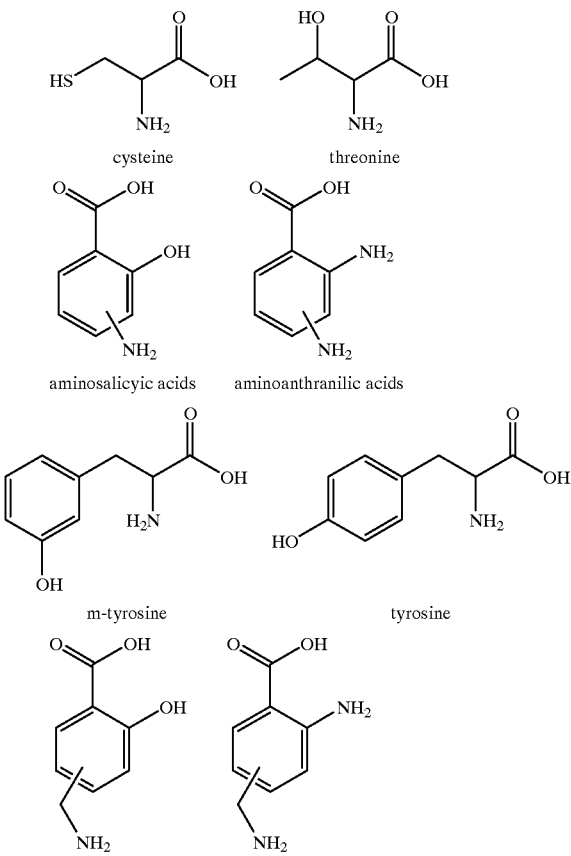

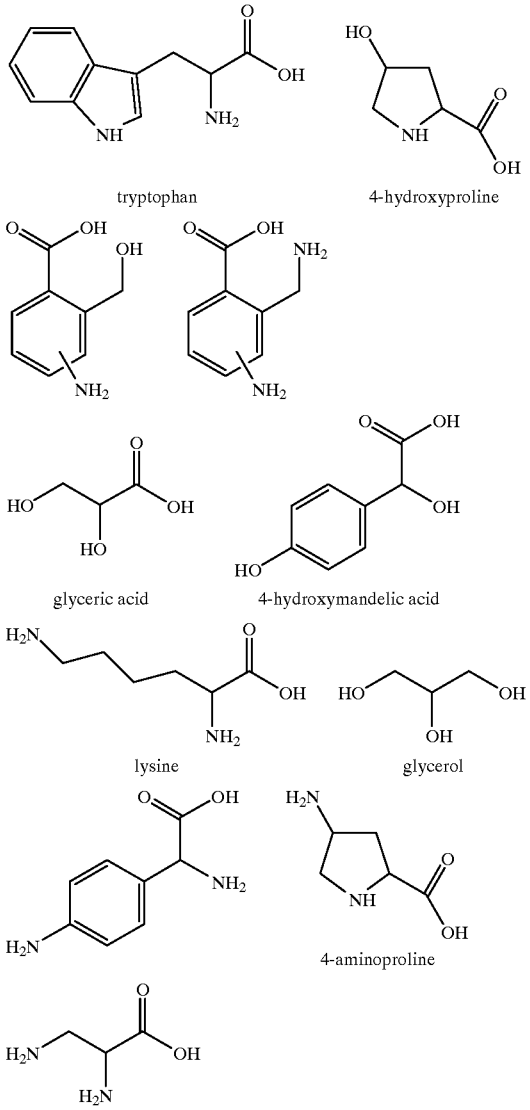

More especially, the trivalent radical T in formula I is derived from lysine. For the trivalent radical, racemates or enantiomers may be used.

The bridging groups $R_{01}$, $R_{02}$ and $R_{03}$ may contain in the chain from 1 to 30 atoms, especially from 1 to 20 atoms and more especially from 1 to 12 atoms selected from the group C, O, S and N. The bridging group is preferably a hydrocarbon radical that may be interrupted by one or more hetero atoms from the group O, S and N and/or by the group —C(O)—. For an adequate intramolecular interaction between fluorophore and ionophore in the same molecule it may be expedient to select short bridging groups $R_{01}$ and $R_{02}$, for example those having from 1 to 6, preferably from 1 to 4, atoms in the chain. For the same reason, the difference in the chain lengths between the bridging groups $R_{01}$ and $R_{02}$ should not be too large and, for example, should be not more than 10, and especially a maximum of 6, more especially a maximum of 4, atoms. An adequate change in the signal will, however, also occur in the case of longer bridging groups, since in that case there is intermolecular interaction between different molecules.

The bridging group $R_{01}$ may correspond to formula (IIa)

$$—X_1—(R_3)_r—X_2—\quad\text{(IIa)},$$

the bridging group $R_{02}$ may correspond to formula (IIb)

$$—X_3—(R_4)_s—X_4—\quad\text{(IIb)},$$

and the bridging group $R_{03}$ may correspond to formula (IIc)

$$—X_5—(R_2)_t—X_7—\quad\text{(IIc)},$$

wherein $X_1$, $X_2$, $X_3$, $X_4$, $X_5$ and $X_7$ are each independently of the others a direct bond, or $X_1$, $X_2$, $X_3$, $X_4$, $X_5$ and $X_7$ are each independently of the others selected from the group —O—, —S—, —NR$_5$—, —C(O)—O—, —O—C(O)—, —O—C(O)—O—, —SO$_2$—O—, —O—SO$_2$—, —O—SO$_2$—O, —NR$_5$—C(O)—, —C(O)—NR$_5$—, —NR$_5$—C(O)—O—, —O—C(O)—NR$_5$—, —NR$_5$—C(O)—NR$_5$—, —NR$_5$SO$_2$—, —SO$_2$—NR$_5$—, —NR$_5$—SO$_2$—O—, —O—SO$_2$NR$_5$— and —NR$_5$SO$_2$—NR$_5$—, $R_5$ is H or $C_1$–$C_{30}$alkyl, $C_5$- or $C_6$-cycloalkyl, $C_5$- or $C_6$-cycloalkyl-methyl or -ethyl, phenyl, benzyl or 1-phenyleth-2-yl, $R_2$, $R_3$ and $R_4$ are each independently of the others a divalent bridging group, r, s and t are each independently of the others 0 or 1, with the proviso that r, s or t is 1 when $X_1$ or $X_3$ or $X_5$ is one of the said groups.

When $R_5$ is alkyl it has preferably from 1 to 6 carbon atoms and especially from 1 to 4 carbon atoms. Examples include methyl, ethyl, n-propyl, isopropyl, butyl, hexyl and octyl. When $R_5$ is cycloalkyl it is preferably cyclohexyl, and when $R_5$ is cycloalkylmethyl it is preferably cyclohexylmethyl. In a preferred embodiment, $R_5$ is H or $C_1$–$C_4$alkyl.

The divalent bridging groups $R_2$, $R_3$ and $R_4$ are preferably hydrocarbon radicals that each independently of the others has preferably from 1 to 30 carbon atoms, more preferably from 1 to 18 carbon atoms, especially from 1 to 12 carbon atoms and more especially from 1 to 8 carbon atoms, and is unsubstituted or mono- or poly-substituted by $C_1$–$C_4$alkyl, $C_1$–$C_4$alkoxy or by =O. The hydrocarbon radical may also be interrupted one or more times by hetero atoms selected from the group —O—, —S— and —NR$_5$— wherein $R_5$ is preferably H or $C_1$–$C_4$alkyl.

The divalent bridging groups $R_2$, $R_3$ and $R_4$ each independently of the others may be, for example, $C_1$–$C_{20}$alkylene, preferably $C_2$–$Cl_{12}$alkylene, which may be linear or branched. Examples include methylene, ethylene, 1,2- and 1,3-propylene, 1,2-, 1,3- and 1,4-butylene, pentylene, hexylene, octylene, dodecylene, tetradecylene, hexadecylene and octadecylene.

The divalent bridging groups $R_2$, $R_3$ and $R_4$ each independently of the others may be, for example, polyoxaalkylene having from 2 to 12, especially from 2 to 6, and more especially from 2 to 4, oxaalkylene units, and from 2 to 4, preferably 2 or 3, carbon atoms in the alkylene radical. $R_2$, $R_3$ and $R_4$ are especially polyoxaethylene or polyoxypropylene having from 2 to 6 oxaalkylene units.

The divalent bridging groups $R_2$, $R_3$ and $R_4$ each independently of the others may be, for example, $C_5$–$C_{12}$-, especially $C_5$–$C_8$- and more especially $C_5$- or $C_6$-cycloalkylene, such as, for example, cyclopentylene, cyclohexylene, cyclooctylene or cyclododecylene.

The divalent bridging groups $R_2$, $R_3$ and $R_4$ may be, for example, $C_5$–$C_{12}$-, especially $C_5$–$C_8$- and more especially $C_5$- or $C_6$-cycloalkyl-$C_1$–$C_{12}$- or preferably -$C_1$–$C_4$-alkyl. Examples include cyclopentyl-$C_nH_{2n}$— and cyclohexyl-$C_nH_{2n}$—, wherein n is from 1 to 4. -Cyclohexyl-$CH_2$— is especially preferred.

The divalent bridging groups $R_2$, $R_3$ and $R_4$ each independently of the others may be, for example, $C_5$–$C_{12}$-, especially $C_5$–$C_8$- and more especially $C_5$- or $C_6$-cycloalkyl-$(C_1$–$C_{12}$alkyl)$_2$- or preferably -$(C_1$–$C_4$alkyl)$_2$. Examples include cyclopentyl-$(C_nH_{2n}$—)$_2$ and cyclohexyl-$(C_nH_{2n}$—)$_2$, wherein n is from 1 to 4. —$CH_2$-Cyclohexyl-$CH_2$— is especially preferred.

The divalent bridging groups $R_2$, $R_3$ and $R_4$ each independently of the others may be, for example, $C_6$–$C_{14}$arylene, especially $C_6$–$C_{10}$arylene, for example naphthylene or more especially phenylene.

The divalent bridging groups $R_2$, $R_3$ and $R_4$ each independently of the others may be, for example, $C_7$–$C_{20}$aralkylene, especially $C_7$–$C_{12}$aralkylene. Arylene-$C_nH_{2n}$— wherein arylene is naphthylene or especially phenylene and n is from 1 to 4, is preferred. Examples are benzylene and phenylethylene.

The divalent bridging groups $R_2$, $R_3$ and $R_4$ each independently of the others may be, for example, arylene-$(C_nH_{2n}$—)$_2$— wherein arylene is preferably naphthylene or especially phenylene and n is from 1 to 4. Examples are xylylene- and phenylene-$(CH_2CH_2)_2$—.

In a preferred embodiment, the bridging group $R_{01}$ is a divalent radical selected from the group —O—, NH, —N($C_1$–$C_4$alkyl)—, —O—C(O)—, —NH—C(O)—, —N($C_1$–$C_4$alkyl)—C(O)—, —C(O)—O, —C(O)—NH, —C(O)—N($C_1$–$C_4$alkyl)—, —O—C(O)—$CH_2$—O—, —NH—C(O)—$CH_2$—O—, —N($C_1$–$C_4$alkyl)—C(O)$CH_2$—O—, —NH—C(O)$CH_2$—NH—, —N($C_1$–$C_4$alkyl)—C(O)$CH_2$—NH—, —O—C(O)—NH—, —NH—C(O)—O— and —NH—C(O)—NH—.

In another preferred embodiment the bridging group $R_{02}$ is a divalent radical selected from the group —O—, NH, —N($C_1$–$C_4$alkyl)—, —O—C(O)—, —NH—C(O)—, —N($C_1$–$C_4$alkyl) —C(O)—, —C(O)—O, —C(O)—NH, —C(O)—N($C_1$–$C_4$alkyl)—, —O—C(O)—$CH_2$—O—, —NH—C(O)—$CH_2$—O—, —N($C_1$–$C_4$alkyl)—C(O)$CH_2$—O—, —NH—C(O)—$CH_2$—NH—, —NH—C(O)—$CH_2$—NH—, —N($C_1$–$C_4$alkyl)—C(O)$CH_2$—NH—, —O—C(O)—NH—, —NH—C(O)—O— and —NH—C(O)—NH—. —NH—C(O) and —C(O)—NH are especially preferred.

In a further preferred embodiment the bridging group $R_{03}$ is a divalent radical selected from the group of open-chained aliphatic radicals having from 2 to 20, preferably from 4 to 20, carbon atoms, which are uninterrupted or are interrupted by one or more atoms or groups selected from —O—, —NH—, —O—C(O)—, —C(O)—O—, —NH—C(O)—, —C(O)—NH—, —NH—C(O)—NH—, —NH—C(O)—O— and —O—C(O)—NH—. Examples are $C_2$–$C_{20}$alkylene, which is uninterrupted or is interrupted by one or more —O— atoms. Alkylene interrupted by —O— is derived preferably from oligoethylene oxides having from 1 to 8, preferably from 2 to 6, oxaethylene units.

Ionophores for specific ions are known in large numbers, the ions frequently being bound by complex formation and/or salt formation. Methods for the introduction of functional groups, if they are not already present, are known to the person skilled in the art.

The ionophores may be, for example, $Ca^{2+}$ ionophores that correspond to the formula

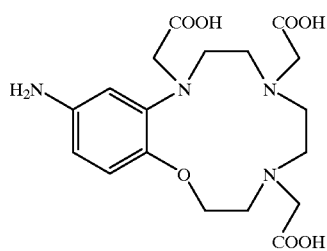

[see *J. Org. Chem.* 1993, 58, 4681–4684], or $Ca^{2+}$ ionophores that correspond to the formula

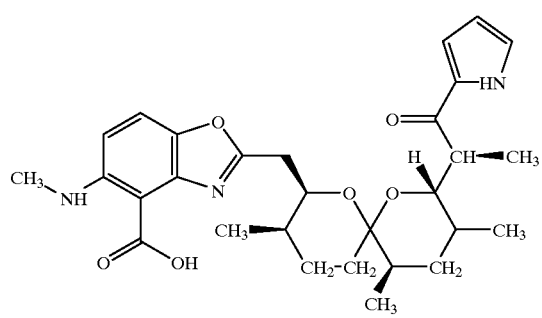

[*J. Am. Chem. Soc.* 1994, 116, 4505–4506], or Na+ ionophores that correspond to the formula

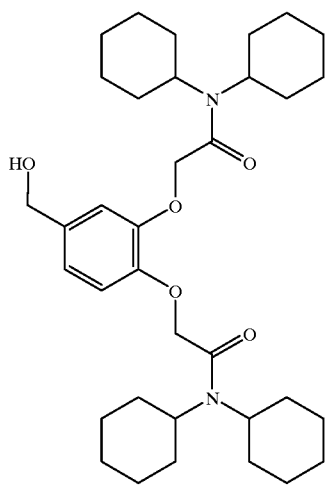

[ETH 4120 analogue *Anal. Chim. Acta* 1990, 233, 295].

The ionophores are preferably 1,3-alternating calix[4] crown-5 compounds of formula IV

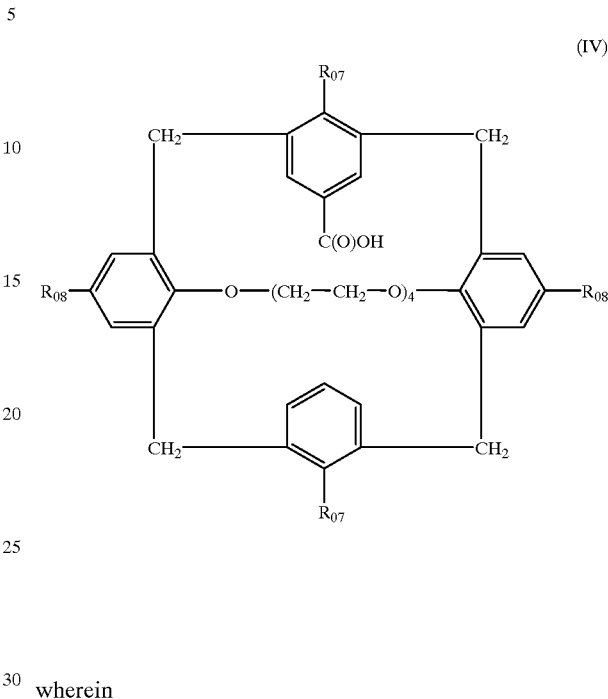

wherein $R_{07}$ and $R_{08}$ are each independently of the other H, linear or branched $C_1$–$C_{20}$alkyl, or linear or branched $C_1$–$C_{20}$alkoxy, or acid derivatives thereof.

$R_{08}$ is preferably H. $R_{07}$ and $R_{08}$ as alkyl and alkoxy contain especially from 1 to 12, and more especially from 1 to 6, carbon atoms. Examples of alkyl are methyl, ethyl and the isomers of propyl, butyl, pentyl, hexyl, heptyl, octyl, nonyl and decyl, and examples of alkoxy are methoxy, ethoxy, propoxy, butoxy, pentyloxy and hexyloxy.

Examples of acid derivatives are the acid halides, especially the acid chlorides and bromides, the acid esters, especially the $C_1$–$C_{18}$alkyl esters, the acid amides, the $NH_2$ group of which may be substituted by $C_1$–$C_4$alkyl, and the salts of, for example, alkali metals, such as sodium or potassium.

The compounds of formula IV and the acid derivatives thereof are novel and the invention relates also to them. Their preparation is described in the Examples.

In another embodiment the ionophores are derived preferably from calix[4]arenes, especially from calix[4]arenes of the formula (IVa)

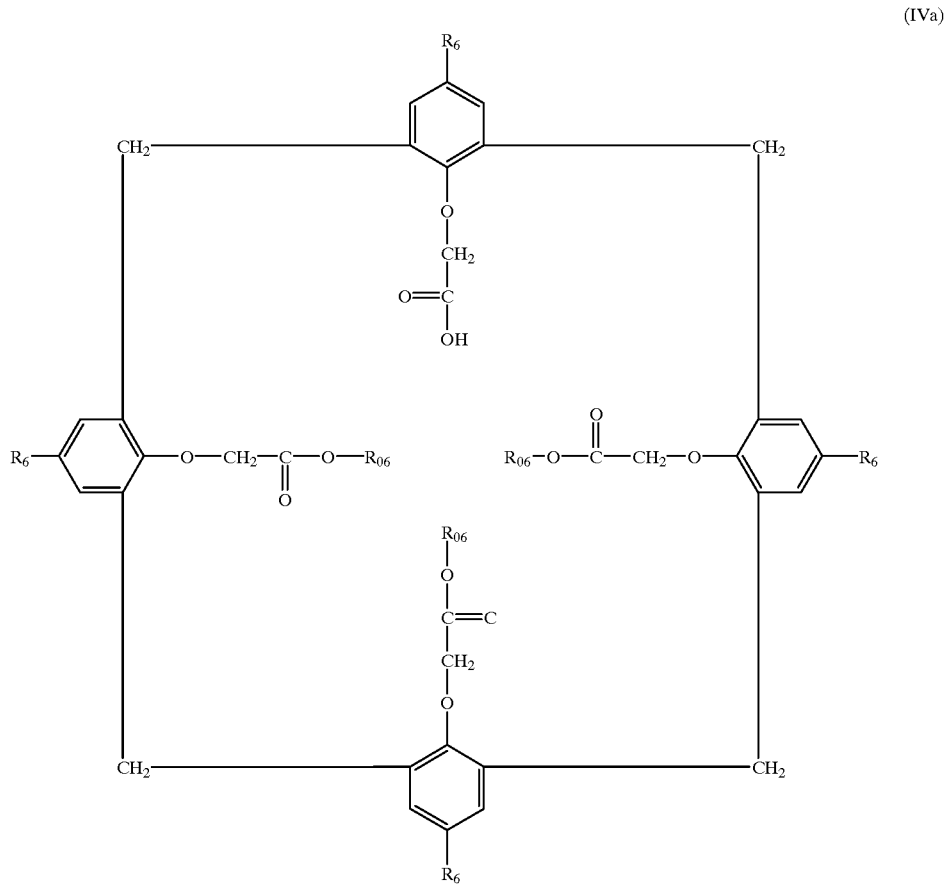

(IVa)

wherein $R_{06}$ is H or substituted or unsubstituted $C_1$–$C_{20}$alkyl, and $R_6$ is H or substituted or unsubstituted $C_1$–$C_{30}$alkyl.

$R_6$ is especially linear or branched $C_1$–$C_{12}$alkyl, more especially linear or branched $C_1$–$C_8$alkyl.

Examples of alkyl are methyl, ethyl and the isomers of propyl, butyl, pentyl, hexyl, heptyl, octyl, nonyl and decyl.

In a preferred embodiment $R_{06}$ is H or $C_1$–$C_4$alkyl.

More especially $R_{06}$ is tertiary butyl or ethyl.

$R_6$ is especially linear or branched $C_1$–$C_{10}$alkyl, more especially linear or branched $C_1$–$C_4$alkyl.

Examples of alkyl are methyl, ethyl and the isomers of propyl, butyl, pentyl, hexyl, heptyl, octyl, nonyl and decyl.

In a preferred embodiment $R_6$ is H or $C_1$–$C_4$alkyl.

More especially $R_6$ is tertiary butyl.

The fluorophores from which F in formula (I) is derived are composed preferably of carbonyl groups, C—C double bonds and aromatic rings, and are more especially condensed ring systems, such as naphthalenes, anthracenes, benzofurans, benzodiazines, benzotrioxazines, benzotriazepines, pyrenes and coumarins.

The fluorophores from which F in formula (I) is derived may be fluorescein or derivatives thereof, for example fluorescein derivatives of the formulae:

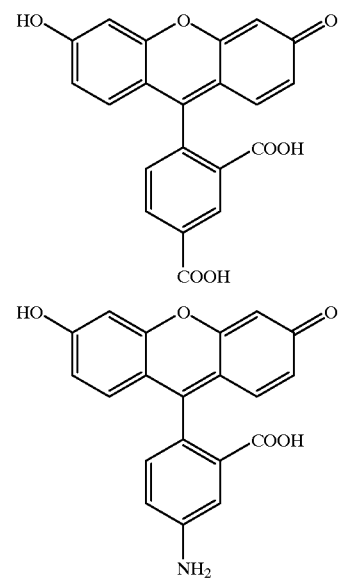

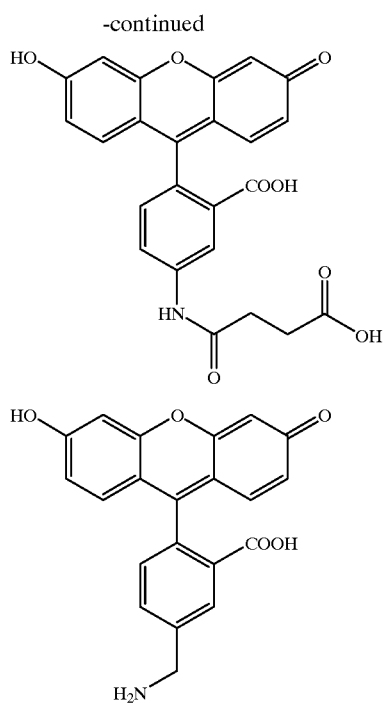
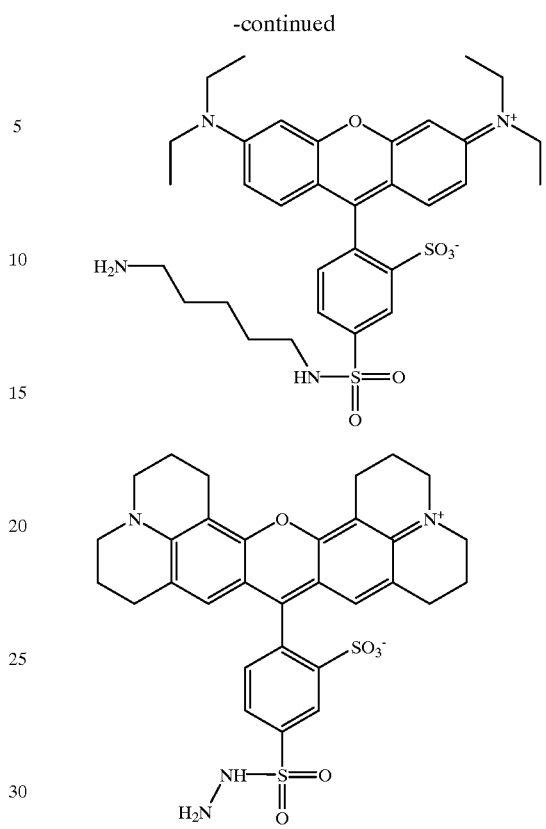
The fluorophores from which F in formula (I) is derived may be rhodamines or benzoxazones or derivatives thereof, for example those of the formulae:
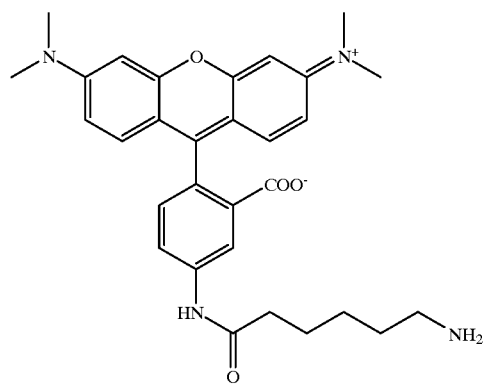
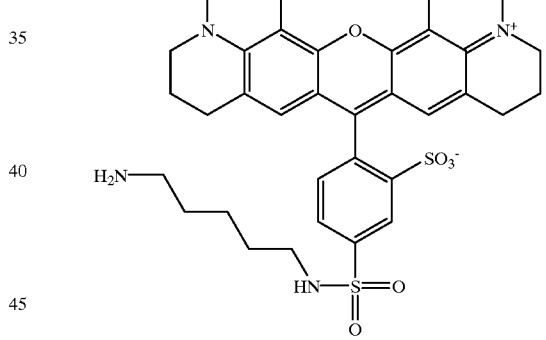
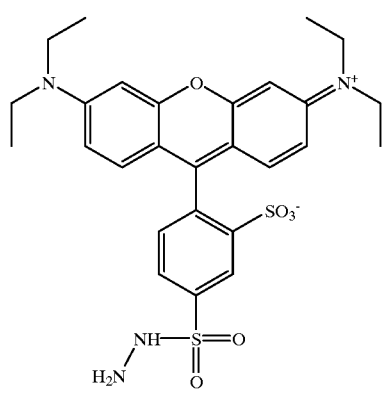
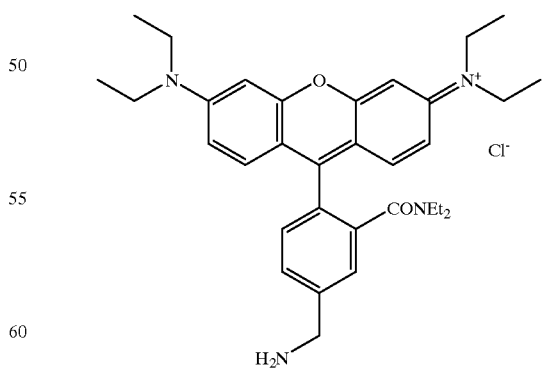

-continued

B
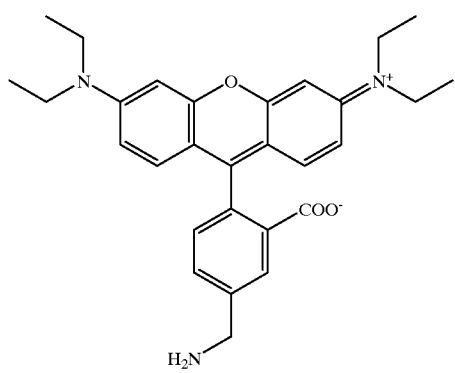

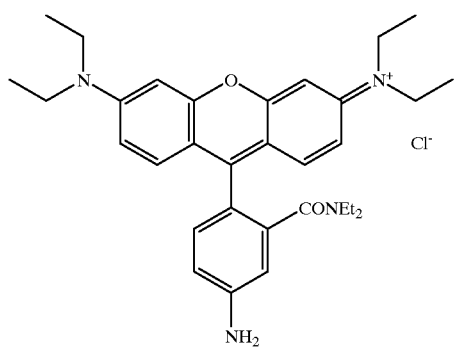

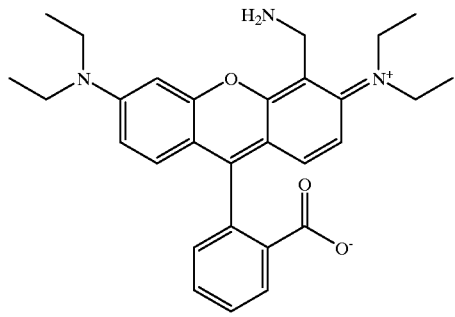

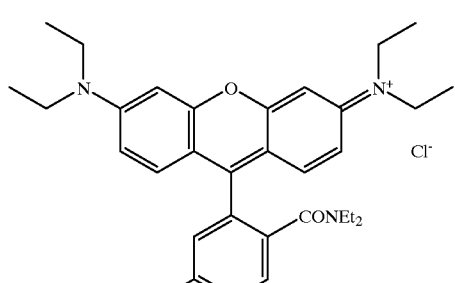

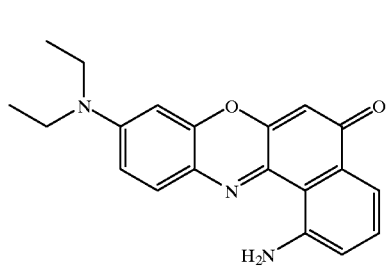

Compounds A–F are novel and their preparation is described in the Examples.

The fluorophores from which F in formula (I) is derived may be acridines or derivatives thereof of the formula:

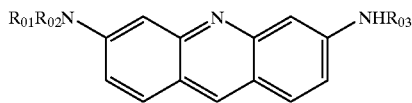

wherein $R_{01}$ and $R_{02}$ are each independently of the other H or $C_1$–$C_{20}$alkyl and $R_{03}$ is H or $C_1$–$C_6$alkyl.

The fluorophores from which F in formula (I) is derived may be carbocyanines, for example of the formula:

C
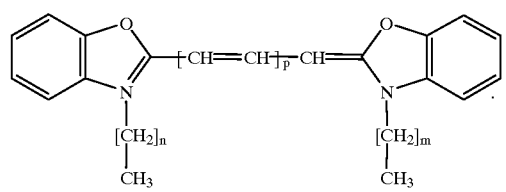

n = 0–20
m = 0–20
p = 0–4

D
The fluorophores from which F in formula (I) is derived may be merocyanines, for example merocyanine 540, or derivatives thereof

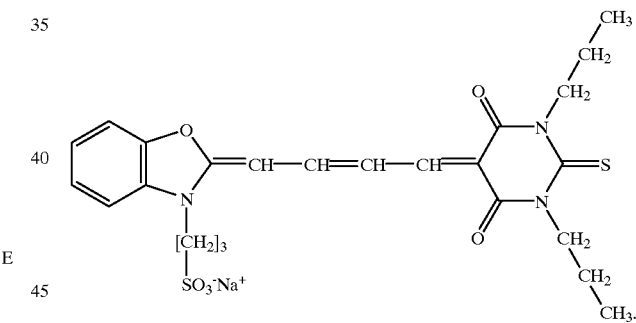

E

The fluorophore is derived preferably from acridines or rhodamines or derivatives thereof, especially from 3,6-diaminoacridines and rhodamines of the formulae F
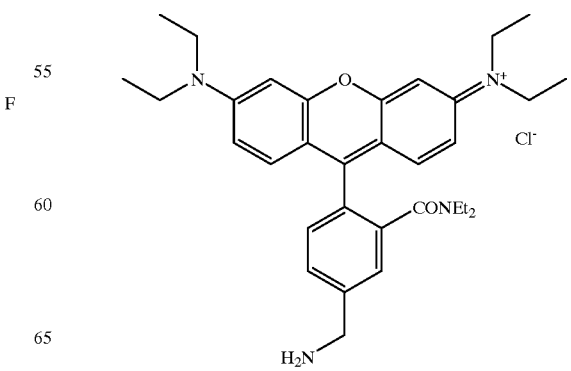

-continued

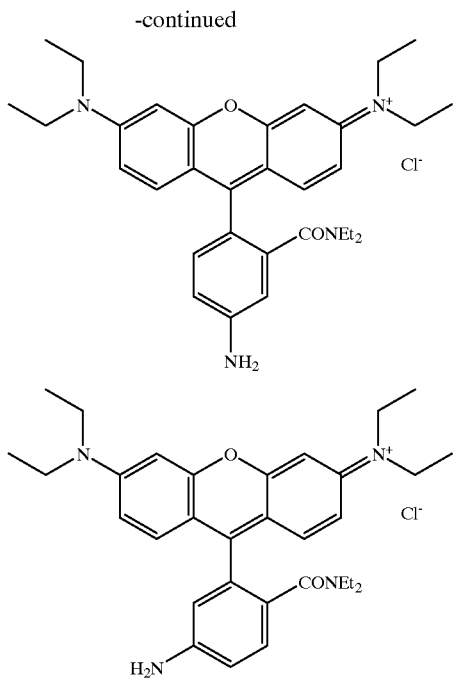

and from the compound of formula

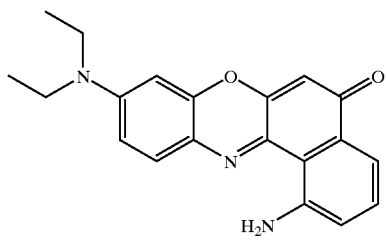

The fluoroionophores of formula I according to the invention are preferably compounds of formula (Ia)

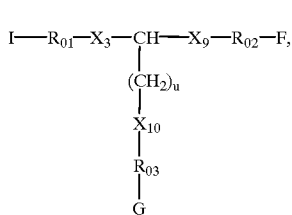

(Ia)

wherein
$X_8$, $X_9$ and $X_{10}$ are each independently of the others —C(O)O—, —OC(O)—, —C(O)NR$_5$— or —NR$_5$—C(O)—, and I, $R_{01}$, $R_{02}$, $R_{03}$, G and F have the meanings and preferred meanings given above in formula (I), u is an integer from 1 to 6 and preferably from 1 to 4, and the $R_5$ radicals are each independently of the other H or $C_1$–$C_4$alkyl. The $R_5$ radicals are preferably H.

In formula Ia $R_{01}$ is preferably a direct bond or —CH$_2$.

In formula Ia $R_{02}$ is preferably a direct bond or $C_1$–$C_6$alkylene.

In formula Ia $R_{03}$ is preferably $C_2$–$C_{20}$alkylene or —CH$_2$—(O—CH$_2$CH$_2$—)$_v$ wherein v is from 1 to 8, especially from 1 to 6 and more especially from 1 to 4.

The fluoroionophores are more especially those of formula Id

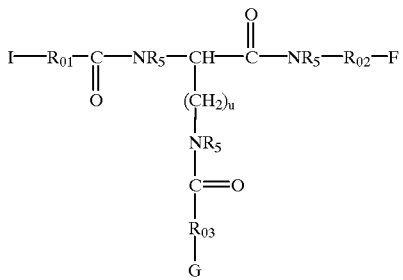

(Id)

wherein
I, $R_{02}$, $R_{03}$, G, F and the $R_5$ radicals have the meanings and preferred meanings given hereinbefore.

There may be mentioned specifically, for example, the following fluoroionophores of the formulae

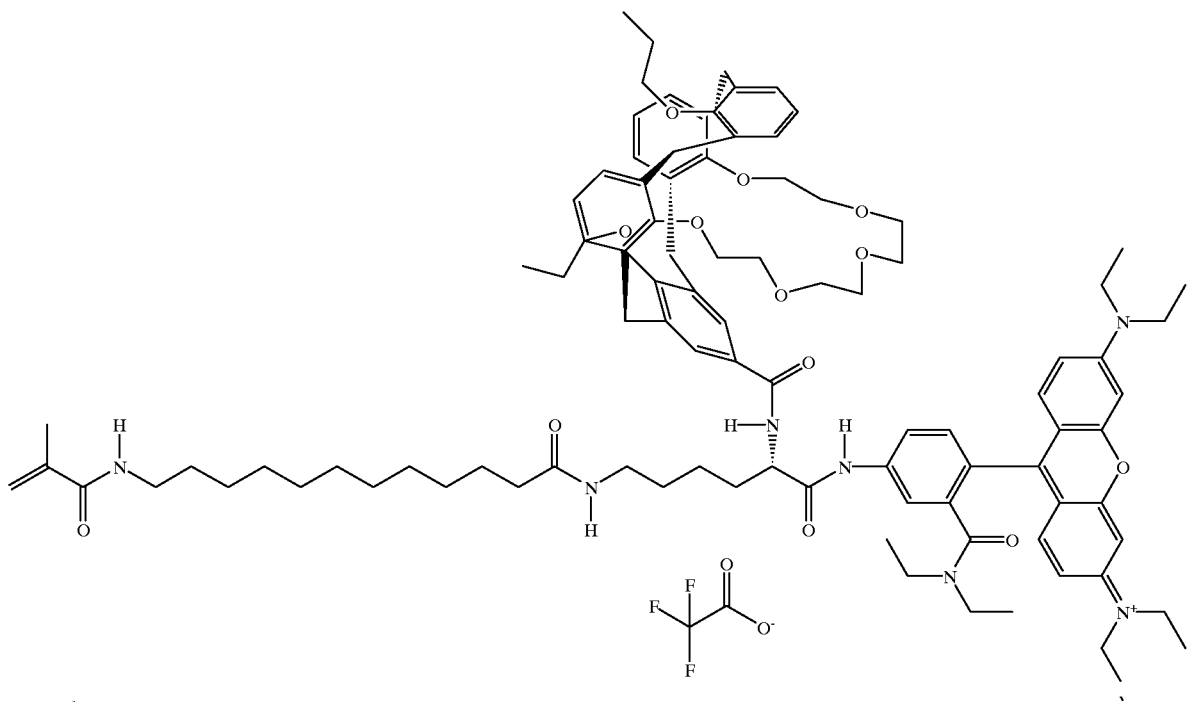
and
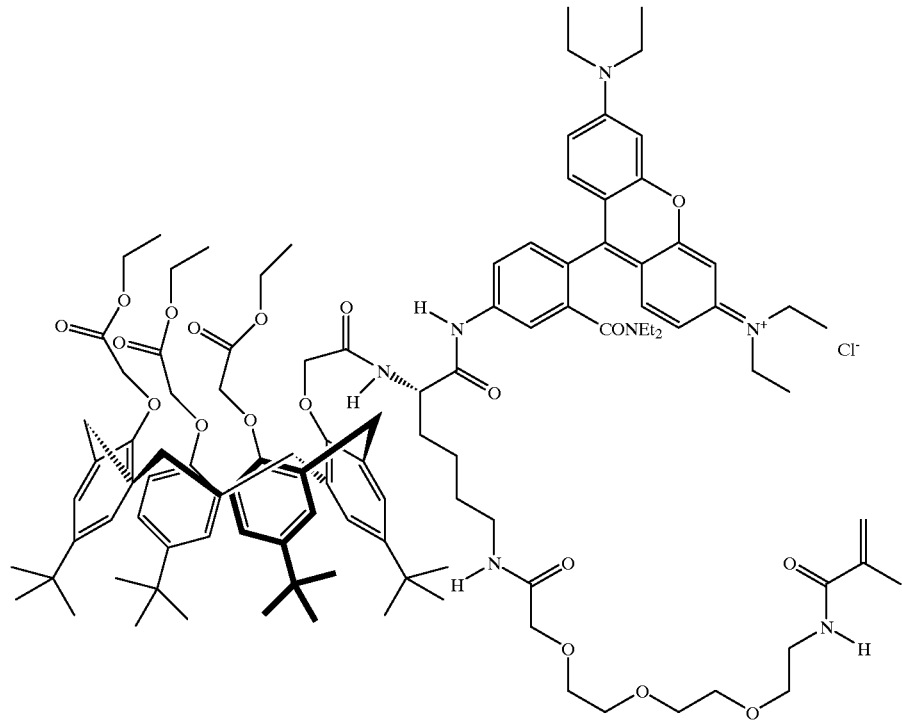
and

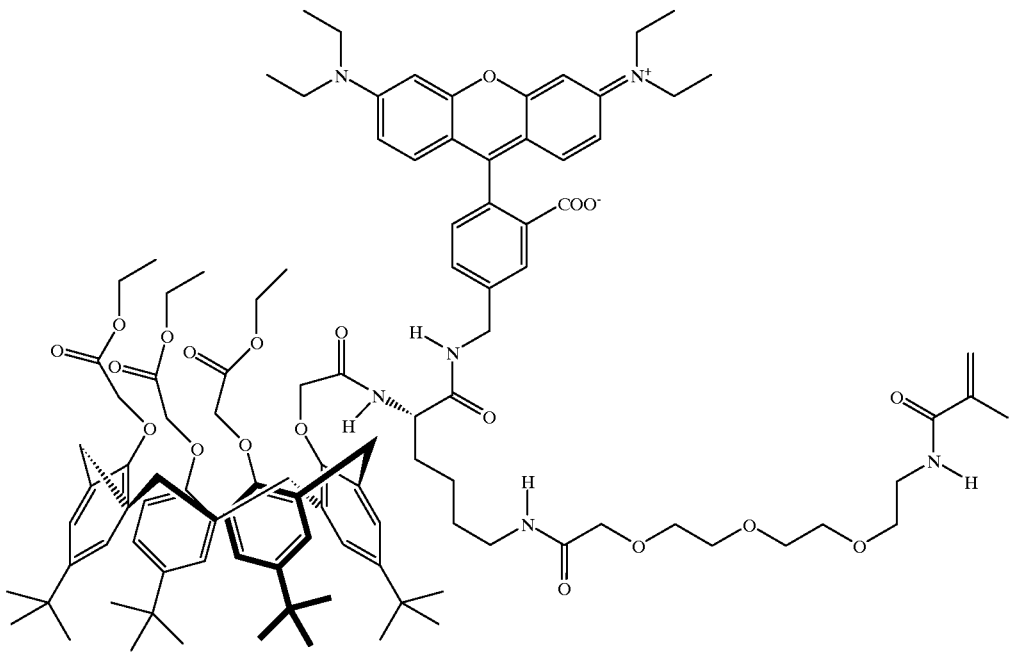

The compounds of formula I may be prepared according to processes known per se, usually using a trifunctional compound of formula Z

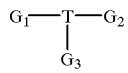

(Z)

as starting material and subsequently introducing bridging groups, where appropriate, and the groups I, F and G in any order by linking their functional group with the functional groups $G_1$, $G_2$ and $G_3$ which are, as the case may be, bonded to bridging groups. Functional groups not required for a reaction step may be protected and removed again in conventional manner.

In order to avoid too many reaction steps, when polymerisable groups are used as functional groups, it has proved expedient to begin with the introduction of the functional group that does not have to be protected.

The invention relates also to a process for the preparation of compounds of formula (I) which comprises reacting a compound of formula Ie

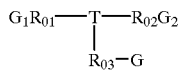

(Ie)

wherein G, $G_1$ and $G_2$ are functional groups and $R_{O1}$, $R_{O2}$ and $R_{O3}$ are a direct bond or a bridging group, the group G and one of the groups $G_1$ and $G_2$ being protected if necessary; either first of all with an ionophore of formula If

(If)

and then with a fluorophore of formula Ig

(Ig);

or first of all with a fluorophore of formula Ig and then with an ionophore of formula If; in which formulae I is the monovalent residue of an ionophore and F is the monovalent residue of a fluorophore, and $G_{O1}$, and $G_{O2}$ are functional groups that react with $G_1$ and $G_2$.

The compounds of formulae Z, Ie and If are known or can be prepared according to known processes.

To prepare a compound of formula (I), a functional group of the compound of formula (Ie) may first of all be protected by a protecting group. In order to link the monofunctional ionophore of formula (If) and the monofunctional fluorophore, the functional groups thereof or the functional group of the compounds of formula Ib may be activated. Known methods of activation are, for example, etherification, esterification, amidation, and urea and urethane formation, for the introduction of readily removable groups. Activation of the functional groups by activated esters is preferred.

The compounds of formulae (Ie), (If) and (Ig) may be used in equimolar amounts.

Protecting groups and methods of derivatising functional groups are known from organic chemistry textbooks (E. Breitmaier, Günther Jung; Organische Chemie II (1983); Georg Thieme Verlag Stuttgart, New York p. 342, 409ff).

The functional groups may be protected, for example, by derivatisation. Functional groups of the —XH type (X=O, S, NH) may be protected by acylation and acyl derivatives or carbonic acid derivatives may thus be prepared. Carboxy-protecting groups are known from peptide synthesis, for example esterification with methanol, ethanol or monomethylethylene glycol ether. Protecting groups for amino functions may be, for example, benzyloxycarbonyl, tert-butoxycarbonyl, p-toluenesulfonyl, 2-nitrophenylsulfenyl, trifluoroacetyl or fluorenylmethoxycarbonyl.

The linkage via functional groups may be carried out in accordance with generally known methods. It is, in principle, also possible to convert any functional groups that are present into different functional groups, for example to convert —CH$_2$OH groups by oxidation into carboxylic acids, carboxylic acids into amides or halides, amine groups into isocyanate groups, and alcohols or amines into carbonates or urethanes. It is also possible for alcohols or amines to be reacted first of all with halocarboxylic acids (for example chloroacetic acid). Chain-extenders, for example epoxides, aziridines, diols, diamines, dicarboxylic acids or esters and diisocyanates, may also be employed one or more times in succession, thus determining the length of the bridging group in a defined manner. Those linkage methods and procedures are known and are described in the specialist literature.

The reactions may be carried out with customary inert organic solvents and at temperatures of, for example, from 0° C. to 200° C.

Suitable inert solvents are, for example, protic polar solvents and aprotic solvents, which may be used alone or in the form of mixtures of at least two solvents. Examples are: water, alkanols (methanol, ethanol, propanol, butanol, ethylene glycol monomethyl or monoethyl ether), ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, methyl propionate, ethyl benzoate, 2-methoxyethyl acetate, γ-butyrolactone, δ-valerolactone, pivalolactone), carboxylic acid amides and lactams (N,N-dimethylformamide, N,N-diethylformamide, N,N-dimethylacetamide, tetramethylurea, hexamethylphosphoric acid triamide, γ-butyrolactam, ε-caprolactam, N-methylpyrrolidone, N-acetylpyrrolidone, N-methylcaprolactam), sultoxides (dimethyl sulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons, for example petroleum ether, pentane, hexane, cyclohexane, methylcyclohexane, benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile).

The compounds of formula (I) may be isolated in customary manner by precipitation, crystallisation or extraction and, where necessary, purified by means of recrystallisation or chromatographic methods.

If acids are formed during the reactions, acid acceptors may be added, for example alkali metal carbonates or tertiary amines, especially sterically hindered tertiary amines.

Further details relating to the preparation of the compound of formula (I) will be found in the Examples.

The compounds of formula I are excellently suitable for the simultaneous covalent bonding of ionophores and fluorophores to carrier materials in order to prevent their being washed out during use. The covalent bonding may be effected, for example, by polymerisation or copolymerisation or by subsequent reaction of functionalised carrier materials with correspondingly functional compounds of formula I.

The invention relates also to a composition comprising (a) an inorganic or organic carrier material to which (b) a fluoroionophore of formula (I) is bonded via the functional group G directly or via a bridging group.

In the case of the fluoroionophores of formula (I) that are covalently linked to the functional groups of a carrier material via their reactive group G, a distinction can be made between two embodiments, namely (A) polymers comprising monomers having covalently bound fluoroionopnores and optionally (B) finely divided inorganic or organic carrier materials that have been subsequently modified on the surface for the covalent bonding of the fluoroionophores. In comparison with the polymers of embodiment (A) in the form of emulsion polymers (latices), embodiment (B) offers the advantage of a lower consumption of fluoroionophores, since the latter have not been partially polymerised into the microparticles and consequently rendered inaccessible.

The embodiments which follow relate to embodiment (B).

The carrier material may be an inorganic or organic carrier material. The carrier material may be opaque, translucent or transparent. Transparent carrier materials are preferred. Opaque or translucent carrier materials may be used, for example, in the preparation of thin layers. Suitable carrier materials are, for example, plastics, glass, ceramics, minerals, stone, metal oxides, metal nitrides, metal carbides, metals and metal alloys. The carrier materials contain functional groups for binding the fluoroionophores, which groups may, if necessary, be produced in a simple manner by plasma treatment, where necessary in a reactive gas atmosphere. Preferred carrier materials are plastics, for example polymers having functional groups, or polymers that have been surface-modified subsequently in order to introduce functional groups, for the covalent bonding of the fluoroionophores.

In the case of inorganic carrier materials, the functional groups are especially amine groups and more especially hydroxyl groups. The functional groups are generally provided with anchor groups to which the fluoroionophores are bonded directly or via a bridging group. Silanes that have a functional group are preferred for that purpose, for example tri($C_1$–$C_4$alkoxy) Si—$(CH_2)_p$—$NH_2$, tri($C_1$–$C_4$alkoxy)Si—$(CH_2)_p$—OH, tri($C_1$–$C_4$alkoxy)Si—$(CH_2)_p$—NH—$CH_2CH_2$—$NH_2$, tri($C_1$–$C_4$alkoxy)Si—$_{(CH_2)_p}$—C(O)OH, tri ($C_1$–$C_4$alkoxy)—(prop-1-en-3-yl)silane, tri-($C_1$–$C_4$alkoxy)-glycidoxysilane and tri($C_1$–$C_4$alkoxy)Si—$(CH_2)_p$—NCO, wherein p is from 2 to 12, especially from 2 to 6 and more especially from 2 to 4. Examples include γ-aminopropyl-trimetnoxy- or -triethoxy-silane, γ-hydroxypropyl-trimethoxy- or -triethoxy-silane and 2-trimethoxy- or 2-triethoxy-silylpropionic acid.

In the case of organic carrier materials, the functional groups are preferably amine, hydroxyl, carboxy, —$SO_3H$ or isocyanate groups. They may be natural or synthetic polymers having functional groups, which polymers have been modified subsequently (for example by means of plasma treatment) or milled. Suitable synthetic polymers include emulsion polymers and latices of at least one monomer having functional groups. Examples of natural polymers are polysaccharides, such as cellulose, starch, carageenan and chitosan, which may have been partially etherified by $C_1$–$C_4$alkyl or partially acylated by $C_1$–$C_8$acyl. Synthetic polymers having functional groups are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, -methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesulfonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Duroplasts are also suitable, for example epoxy resins, melamine-formaldehyde resins and phenol-formaldehyde resins. Suitable comonomers are, for example, olefins, such as ethene, propene, butene, pentene, octene; vinyl chloride, vinylidene chloride; styrene; and acrylonitrile. Also suitable are crosslinked polymers, for example polymerisates having olefinic and diolefinic monomers, such as butadiene, divinylbenzene or dioldiacrylic or -methacrylic acid esters. Other suitable vinyl polymers are polyvinylpyrrolidone, polyvinylimidazole and polyvinylpyridine and copolymers having unsubstituted or substituted olefins as comonomers.

The amount of fluoroionophore covalently bound to the carrier material may be, for example, from 0.0001 to 99% by weight, preferably from 0.001 to 80% by weight, more preferably from 0.001 to 50% by weight, especially from 0.1 to 20% by weight, and more especially from 1 to 10% by weight, based on the carrier material.

In a preferred embodiment, there are ionically or covalently bound to the carrier material, in addition, radically or cationically photopolymerisable organic radicals that preferably correspond to the polymerisable organic compounds used for the preparation of a sensor membrane. Accordingly, in radically polymerisable ethylenically unsaturated systems it is advantageous to use ethylenically unsaturated compounds having functional groups and, in cationically polymerisable systems, such as, for example, di- or poly-epoxides, it is expedient to use di- or poly-epoxides having functional groups.

Ethylenically unsaturated organic compounds having functional groups, which are known in large numbers, are preferred. The residues, covalently bound to the carrier material, of ethylenically unsaturated organic compounds may correspond, for example, to formula VI

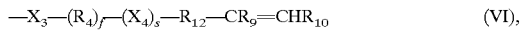

$$-X_3-(R_4)_r-(X_4)_s-R_{12}-CR_9=CHR_{10} \qquad (VI),$$

wherein $X_3$ is —NR$_5$— in which $R_5$ is H, $R_4$ is $C_1$–$C_{18}$alkylene, especially $C_1$–$C_8$alkylene and more especially $C_1$–$C_3$alkylene, $X_4$ is —NR$_{04}$—C(O)— in which $R_{04}$ is H or $C_1$–$C_8$alkyl, preferably H, and r is 1, $R_{12}$ is a direct bond, $C_1$–$C_{18}$alkylene, $C_5$- or $C_6$-cycloalkylene, $C_6$–$C_{10}$arylene or $C_7$–$C_{12}$aralkylene, $R_9$ is H or $C_1$–$C_4$alkyl, especially methyl, and $R_{10}$ is H, $C_1$–$C_{12}$alkyl, phenyl or benzyl.

$R_{12}$ as alkylene contains especially from 1 to 12 and more especially from 1 to 6 carbon atoms. Especially preferred examples are methylene, ethylene, 1,2- and 1,3-propylene and 1,2-, 1,3- and 1,4-butylene. $R_3$ as arylene is preferably phenylene and as aralkylene is preferably benzylene.

$R_9$ is preferably H or methyl, and $R_{10}$ is preferably H.

Ethylenically unsaturated compounds containing functional groups are, for example, ethylenically unsaturated alcohols, amines and isocyanates, such as, for example, allyl alcohol, allylamine, allyl isocyanate. crotonyl alcohol; monoesters or monoamides of dicarboxylic acids and of unsaturated alcohols and amines; functional styrenes, for example chloromethylstyrene, hydroxystyrene, hydroxyethoxystyrene, styreneamine, styrenehydroxyethylamine, styrenecarboxylic acid, styrenesulfonic acid, vinyl hydroxyethyl ether, acrylic acid, methacrylic acid, acrylic or methacrylic acid amide, acrylic or methacrylic acid $C_2$–$C_6$hydroxyalkyl amides and acrylic or methacrylic acid $C_2$–$C_6$hydroxyalkyl esters.

The amount of ionically or covalently bound radically or cationically photopolymerisable organic compounds may be, for example, from 0.001 to 99% by weight, preferably from 0.01 to 80% by weight, more preferably from 0.01 to 50% by weight, especially from 0.01 to 20% by weight, and more especially from 0.1 to 20% by weight, based on the carrier material.

The percentages by weight always add up to 100%.

The immobilisation may be carried out according to generally known processes. "Immobilisation" denotes a covalent bonding, during which it is in principle also possible to convert any functional groups that are present into different functional groups, for example to convert —CH$_2$OH groups by oxidation into carboxylic acids, carboxylic acids into amides or halides, amine groups into isocyanate groups, and alcohols or amines into carbonates or uretnanes. It is also possible for alcohols or amines to be reacted first of all with halo-carboxylic acids (for example chloroacetic acid). Chain extenders, for example epoxides, aziridines, diols, diamines, dicarboxylic acids or esters and diisocyanates, may also be employed one or more times in succession, thus determining the length of the bridging group in a defined manner. Those immobilisation methods and procedures are known and are described in the specialist literature. The bridging group may be built on starting from the carrier material or from the functional compound. The subsequent reaction with the functional compound or carrier material, as the case may be, results in the immobilised fluoroionophores according to the invention. The reactions may be carried out with customary inert organic solvents and at temperatures from 0° C. to 200° C.

"Finely divided" means that particles have a preferably small mean diameter; the diameter of the particles may be from 5 nm to 100 μm, preferably from 10 nm to 50 μm, especially from 10 nm to 20 μm, and more especially from 20 nm to 100 nm.

The following comments relate to embodiment (A):

In another preferred embodiment of the invention the immobilised fluoroionophore is a polymer to the backbone of which monovalent residues of identical or different fluoroionophores are covalently bound directly or via a bridging group. Those polymers may be in the form of heterogeneous particles that are incorporated in a sensor membrane during its manufacture but they may alternatively, and preferably, be soluble polymers from which sensor membranes can be produced directly. The polymer may furthermore be crosslinked and form a layer or membrane.

The polymers may have monomer units comprising monovalent residues of a fluoroionophore and, if desired, comonomer units. The fluoroionophore may be bonded to the monomer directly or via a bridging group and, additionally, spacer groups The bridging groups are derived from functional groups bonded to the monomer (or to the polymer, as the case may be).

In the case of polymers the functional groups are preferably amine, hydroxyl, carboxy, —SO$_3$H or isocyanate groups. The polymers may be milled natural or synthetic polymers having functional groups. Suitable synthetic polymers include emulsion polymers and latices of at least one monomer having functional groups. Examples of natural polymers are polysaccharides, such as cellulose, starch, carrageenan or chitosan, which may have been partially etherified by $C_1$–$C_4$alkyl or partially acylated by $C_1$–$C_8$acyl. Synthetic polymers having functional groups are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, -methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesultfonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Other suitable polymers are polyvinylpyridine, polyvinylimidazole and polyvinylpyrrolidone and copolymers having unsubstituted or substituted olefins as comonomers.

Polymers based on functionally substituted ethylenically unsaturated monomers are preferred.

In a preferred embodiment, the polymers according to the invention contain from 100 to 0.001 mol % of identical or different structural units of formula VII

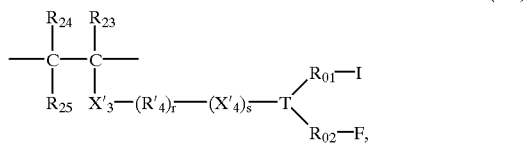

(VII)

and from 0 to 99.9 mol % of identical or different structural units of formula VIII

(VIII)

in which formulae $X'_3$ is —C(O)O— or —C(O)NR$_5$— in which $R_5$ is H, $X'_4$ is —NR'$_4$—C(O)— in which R'$_4$ is H or $C_1$–$C_8$alkyl, preferably H, s is 0 or 1 and r is 0 or 1, r being 1 when s is 0, $R_{O1}$, and $R_{O2}$ are each independently of the other a direct bond or a bridging group, R'$_4$ is a bridging group, I— is the monovalent residue of an ionophore and —F is the monovalent residue of a fluorophore, $R_{23}$ and $R_{24}$ are each independently of the other H, $C_1$–$C_6$alkyl, $C_6$–$C_{10}$aryl or $C_7$–$C_{12}$aralkyl, $R_{25}$ is H or the group —C(O)O—$R_{30}$, $R_{26}$ is H, $C_1$–$C_6$alkyl, $C_6$–$C_{10}$aryl or $C_7$–$C_{12}$aralkyl, $R_{27}$ is H, F, Cl, CN, $C_1$–$C_6$alkyl or $C_6$–$C_{10}$aryl, $R_{28}$ is H, $C_1$–$C_6$alkyl or —C(O)O—$R_{29}$, $R_{29}$ is H, $C_1$–$C_6$alkyl, $C_6$–$C_{10}$aryl, $C_7$–$C_{12}$aralkyl, imidazolyl, pyrrolidonyl, F, Cl, CN or the group $X_1$—$(R_1)_r$—$(X_2)_s$—H, and $R_{30}$ is H, K, Na, $C_1$–$C_{18}$alkyl, $C_1$–$C_{18}$hydroxyalkyl, cyclohexyl, cyclopentyl, cyclohexylmethyl, phenyl, $C_1$–$C_4$alkylphenyl, benzyl or $C_1$–$C_4$alkylphenylbenzyl.

The preferred meanings and embodiments indicated hereinbefore apply to $R_{O1}$, $R_{O2}$, T, I and F.

R'$_4$ is preferably $C_1$–$C_{20}$alkylene, especially $C_1$–$C_{12}$alkylene and more especially $C_1$–$C_8$-alkylene, which may be interrupted by one or more groups selected from —O—, —NH—, —C(O)—O— and —C(O)—NH. R'$_4$ is especially preferably $C_2$–$C_{18}$alkylene, or oligooxaethylene having from 1 to 8 and preferably from 2 to 6 oxaethylene units.

$R_{23}$ and $R_{24}$ as alkyl are preferably $C_1$–$C_4$alkyl, for example methyl, ethyl, n- or iso-propyl or n-, iso- or tert-butyl, as aryl are preferably naphthyl or phenyl and as aralkyl are preferably benzyl. More especially $R_{23}$ is H and $R_{24}$ is H or methyl.

$R_{25}$ is preferably H, —C(O)OH or —C(O)O—$C_1$–$C_4$alkyl.

$R_{26}$ as alkyl is preferably $C_1$–$C_4$alkyl, for example methyl, ethyl, n- or iso-propyl or n-, iso- or tert-butyl, as aryl is preferably naphthyl or phenyl and as aralkyl is preferably benzyl. More especially $R_{26}$ is H.

$R_{27}$ as alkyl is preferably $C_1$–$C_4$alkyl, for example methyl, ethyl, n- or iso-propyl or n-, iso- or tert-butyl, and as aryl is preferably phenyl or naphthyl. More especially $R_{27}$ is H, Cl, CN, phenyl or $C_1$–$C_4$alkyl.

$R_{28}$ as alkyl is preferably $C_1$–$C_4$alkyl, for example methyl, ethyl, n- or iso-propyl or n-, iso- or tert-butyl. $R_{30}$ in the group —C(O)O—$R_{30}$ is especially H or $C_1$–$C_{12}$alkyl, more especially $C_1$–$C_6$alkyl, such as, for example, methyl, ethyl, propyl, butyl, pentyl, hexyl, heptyl, octyl, nonyl, decyl, undecyl, dodecyl, tetradecyl, hexadecyl or octadecyl. More especially $R_{28}$ is H, —C(O)OH or —C(O)—O—$C_1$–$C_4$alkyl.

$R_{29}$ as alkyl is preferably $C_1$–$C_4$alkyl, for example methyl, ethyl, n- or iso-propyl or n-, iso- or tert-butyl, as aryl is preferably phenyl or naphthyl and as aralkyl is preferably benzyl. $R_{29}$ is preferably H, $C_1$–$C_4$alkyl, phenyl, pyrrolidonyl, F, Cl, CN or the group $X_3$—$(R_4)_r$—$(X_4)_s$—H. $R_{29}$ may be, for example, H, K, Na, $C_1$–$C_6$alkyl, $C_1$–$C_6$hydroxyalkyl, cyclohexyl, cyclopentyl, cyclohexylmethyl, phenyl, methylphenyl, benzyl or methylphenylbenzyl.

The structural units of formula VII may be present in an amount of from 0.001 to 100 mol %, especially from 0.5 to 90 mol %, more especially from 0.5 to 80 mol %, more especially from 1 to 80 mol %. more especially from 1 to 60 mol %, more especially from 1 to 50 mol %, and most especially from 1 to 30 mol %.

The structural units of formula Vil may be present in an amount of from 99.9 to 0 mol %, especially from 99.5 to 0 mol %, more especially from 99.5 to 20 mol %, more especially from 99 to 20 mol %, more especially from 99 to 40 mot %, more especially from 99 to 50 mol %, and most especially from 99 to 30 mol %.

The polymers may also contain structural units having pendant unsaturated groups that are used for the crosslinking in the membrane formation.

Structural units of ethylenically unsaturated organic compounds having covalently bound olefin groups, which are known in large numbers, are preferred. The residues, covalently bound to the polymer, of ethylenically unsaturated organic compounds may correspond, for example, to structural units of formula X

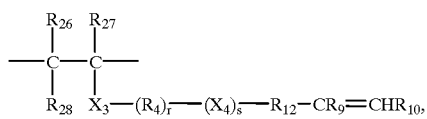

(X)

wherein $X_3$, $X_4$, $R_4$, $R_{12}$, r and s each independently of the others has the meanings and preferred meanings indicated hereinbefore for formula VI, $R_9$ is H or $C_1$–$C_4$alkyl, especially methyl;

$R_{10}$ is H, $C_1$–$C_{12}$alkyl, phenyl or benzyl; and $R_{26}$ $R_{27}$ and $R_{28}$ are as defined for formula VIII.

$R_{12}$ as alkylene contains especially from 1 to 12 and more especially from 1 to 6 carbon atoms. Especially preferred examples are methylene, ethylene, 1,2- and 1,3-propylene and 1,2-, 1,3- and 1,4-butylene. $R_3$ as arylene is preferably phenylene and as aralkylene is benzylene. $R_9$ is preferably H or methyl, and $R_{10}$ is preferably H.

The structural units of formula X may replace from 0.1 to 99.9999 mol %, especially from 0.5 to 90 mol %, more especially from 0.5 to 80 mol %, more especially from 1 to 80 mol %, more especially from 1 to 60 mol %, more especially from 1 to 50 mol %, and most especially from 1 to 30 mol %, of the structural units of formula VIII.

Further, the polymers according to the invention may be crosslinked with at least difunctional monomers, for example with from 0.01 to 30 mol %, preferably from 0.1 to 15 mol %, of such monomers based on the polymer. Depending on the nature of the polymer, there may be used for that purpose at least trifunctional carboxylic acid, isocyanates, alcohols, amines or epoxides and, in the case of polymeric materials, organic compounds containing at least two ethylenically unsaturated groups. Such crosslinking agents are known in large numbers. Ethylenically unsaturated crosslinking agents may be, for example, divinylbenzene, bis-dimethylmaleimide-alkylene (for example bis(dimethylmaleimidyl)-methylene or -ethylene), acrylic acid or methacrylic acid esters or amides of polyols, preferably diols to tetrols, or of polyamines, preferably diamines to tetramines. Aliphatic, cycloaliphatic and cycloaliphatic-aliphatic diols and diamines having especially from 2 to 12, more especially from 2 to 8, carbon atoms are preferred. Examples of such dieos include alkylenediols, such as ethylene glycol, 1,2- and 1,3-propanediol, 1,2-, 1,3- and 1,4-butanediol, pentanediol, hexanediol, octanediol, decanediol, dodecanediol, cyclo-hexanediol, di(hydroxymethyl)-cyclohexane, polyoxaalkylene glycols of alkylenediols, preferably $C_2$–$C_6$alkylenediols, having especially from 2 to 100 alkylenediol units, more especially from 2 to 50 alkylenediol units and most especially from 2 to 20 alkylenediol units, such as, for example, polyethylene glycols, polypropylene glycols, polybutylene glycols and polyethylene/polypropylene glycols, also 1,1,1-trihydroxymethyl-ethane or -propane, pentaerythritol and dipentaerythritol. Examples of polyamines include ethylenediamine, 1,2- and 1,3-propanediamine, 1,2-, 1,3- and 1,4-butanediamine, 1,6-hexanediamine, diethylenetriamine, triethylenetetramine, cyclohexanediamine, aminomethylcyclohexanamine, isophoronediamine and di(aminomethyl)cyclohexane.

In a preferred embodiment the polymers according to the invention comprise at least one structural unit of formula XI

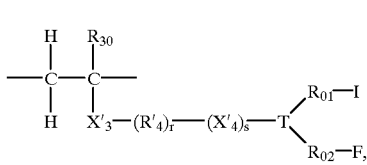

(XI)

wherein $R_{30}$ is H or methyl, and $X'_3$, $X'_4$, $R'_4$, —$R_{02}F$, —$R_{01}$—, T, r and s have the meanings indicated hereinbefore, including the preferred meanings and special embodiments indicated hereinbefore.

The group —$X'_3$—$(R'_4)_r$—$(X'_4)_s$— in the structural units of formula XI is preferably —C(O)—O—, —C(O)—NH—, —C(O)—NH—$C_1$–$C_{12}$alkylene—O—$CH_2$—C(O)—NH—, —C(O)—O—$C_1$–$C_{12}$alkylene—O—$CH_2$—C(O)—NH—, —C(O)—O—($C_2$–$C_6$alkylene—O)$_u$—$CH_2$—C(O)—NH— in which u is from 2 to 10, or —C(O)—NH—($C_2$–$C_6$alkylene-O)$_u$—$CH_2$—C(O)—NH— in which u is from 2 to 10.

The preferred polymeric materials may comprise, in addition to the structural units of formula XI, also identical or different structural units of formula XII

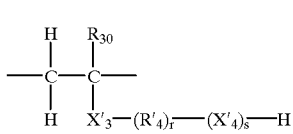

(XII)

wherein $R_{30}$, $X'_3$, $X'_4$, $R'_4$, r and s are as defined hereinbefore. Those structural units are present especially when the compound of formula (I) is reacted with a polymer having functional groups.

The preferred polymeric materials may comprise, in addition to the structural units of formula XI, also identical or different structural units of formula XIII

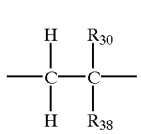

(XIII)

wherein $R_{30}$ is H or methyl, and $R_{38}$ is H, $C_1$–$C_4$alkyl, $C_1$–$C_4$alkoxy, —CN, Cl, phenyl, pyrrolidonyl, pyridinyl, imidazolyl, —C(O)O$R_{39}$ or —C(O)—N$R_{40}R_{41}$, $R_{39}$ is H or $C_1$–$C_{18}$- or preferably $C_1$–$C_{12}$—alkyl, and $R_{40}$ and $R_{41}$ are each independently of the other H or $C_1$–$C_{12}$- or preferably $C_1$–$C_6$-alkyl.

In a further preferred embodiment, the polymeric materials according to the invention having structural units of formula XI and, if desired, of formulae XII and XII, are crosslinked with identical or different structural units of formula XIV or XV

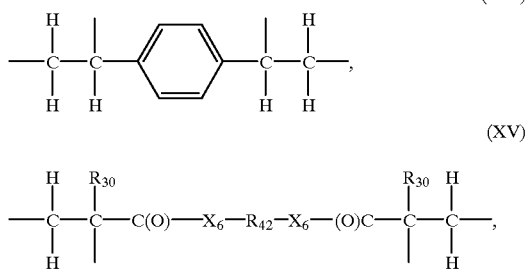

wherein
$R_{30}$ is H or methyl,
$X_6$ is —O— or —NH— or —N($C_1$–$C_4$alkyl)—, and
$R_{42}$ is $C_2$–$C_{12}$- or preferably $C_1$–$C_6$-alkylene, cyclohexylene or cyclohexylenedimethylene, or
$X_6$ is —O— and $R_{42}$ is $C_2$–$C_6$alkylene-($C_2$–$C_6$alkylene—O)$_{2 \, to \, 20}$$C_2$–$C_6$alkylene.

In a further preferred embodiment, the polymeric materials according to the invention having structural units of formula XI and, it desired, of formulae XII, XIII, XIV and XV, comprise identical or different structural units that contain ionic groups, such as, for example —C(O)O$^-$ or —SO$_3^-$ or ammonium groups, bonded in side chains or comprise at least two ion-forming structural units, for example structural units having amino groups and structural units having —C(O)O$^-$ or —SO$_3^-$ bonded in side chains. Those polymers are preferably emulsion polymers or a latex.

The polymers having the structural units of formula X contain those structural units preferably in an amount of from 0.1 to 30% by weight, preferably from 2 to 15% by weight, based on the polymer.

The structural units of formula XII may be present in an amount of from 99 to 0% by weight, preferably from 98 to 0% by weight. The structural units of formula XII may be present in an amount of from 99.9 to 0% by weight, preferably from 98 to 0% by weight. The structural units of formulae XIV and XV may be present in an amount of from 0.1 to 30% by weight, preferably from 1 to 15% by weight.

The polymers according to the invention having structural units of formula VII or XI are preferably emulsion polymers.

The polymers of the invention may be prepared according to procedures known in polymer chemistry. The monomers are known or may be prepared according to known procedures. Known polymerisation processes are solution polymerisation, bulk polymerisation, emulsion polymerisation and interfacial polymerisation. Advantageously, emulsion polymerisation at high stirring speeds is used, since the immobilised fluoroionophores of the invention can be produced in the form of microparticies and subsequent treatments, such as, for example, milling, can be avoided. The milling of polymers for the preparation of microparticles is also generally known, with ball mills, for example, being suitable. In order to protect the polymers, the milling can be carried out with cooling. The preparation of the microparticles may also be carried out in solution, as described hereinbefore for the modification of surfaces in a heterogeneous reaction, by the reaction of natural or synthetic polymers having functional groups and functionalised fluoroionophores and, if desired, other functionalised compounds, for example functional polymerisable compounds. Microparticles can then be obtained by precipitation from the solutions or by milling the isolated modified polymers. In that preparation process the known methods for introducing spacer groups (spacers) may also be used. It is especially also possible for polymers having structural units of formula VII and other structural units having functional groups subsequently to be modified at the surface and, in addition, for polymerisable groups to be bonded covalently only to the surface of the microparticles.

The fluoroionophores according to the invention are excellently suitable per se as active components in optical ion sensors for the detection of ions by means of a change in fluorescence.

The invention relates also to compositions comprising a polymer Z in which an effective amount of at least one compound of formula I is incorporated.

The amount of compound of formula I may be from 0.001 to 10% by weight, especially from 0.01 to 5% by weight, and more especially from 0.01 to 3% by weight, based on the polymer.

The invention relates also to compositions comprising a polymer of embodiment A having a covalently bound fluoroionophore, alone or in admixture with a polymer Z.

The invention relates also to a composition comprising a polymer Z in which a finely divided inorganic or organic carrier material of embodiment B is incorporated.

Those compositions and the polymers of embodiment A, where appropriate in dissolved form, are excellent coating compositions for the manufacture of sensors.

The amount of covalently bound fluoroionophores, polymers or carrier materials may be, for example, from 0.1 to 80% by weight, preferably from 0.1 to 50% by weight, especially from 1 to 20% by weight, more especially from 1 to 10% by weight, based on the composition.

The polymer Z may be a natural or synthetic polymer. Examples of natural polymers are polysaccharides, such as cellulose, starch, carrageenan or chitosan, which may have been partially etherified by $C_1$–$C_4$alkyl or partially acylated by $C_1$–$C_8$acyl. Synthetic polymers are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, -methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesultonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Duroplasts are also suitable, for example epoxy resins, melamine-formaldehyde resins and phenol-formaldehyde resins. Suitable comonomers are, for example, olefins, such as ethene, propene, butene, pentene, octene; vinyl chloride, vinylidene chloride; styrene; and acrylonitrile. Also suitable are crosslinked polymers, for example polymerisates having olefinic and diolefinic monomers, such as butadiene, divinylbenzene or diol-diacrylic or -methacrylic acid esters. Other suitable vinyl polymers are polyvinylpyrrolidone, polyvinylimidazole and polyvinylpyridine and copolymers having unsubstituted or substituted olefins as comonomers.

The compositions according to the invention may comprise solvents and other processing ingredients; solvents have been mentioned hereinbefore. The solvents can be used to adjust the viscosity for the coating processes.

The compositions may be applied to suitable support materials directly or in dissolved form.

The invention relates also to a material comprising (a) a support and (b) an active layer on at least one surface, wherein the active layer consists (1) of a polymer according to the invention, alone or in admixture with a polymer Z, or (2) of a polymer Z in which particles of the polymer according to the invention of embodiment B or of the carrier material of embodiment A are incorporated.

The support is preferably transparent and may be formed, for example, from a plastics material, such as, for example, polycarbonate or acrylic glass, mineral materials, metal oxides or glass, and may be of any shape, for example in the form of plates, cylinders, tubes, strips or fibres. Glasses are preferred.

The thickness of the layer on the support may be, for example, from 0.01 to 100 $\mu$m, preferably from 0.1 to 50 $\mu$m, especially from 0.1 to 30 $\mu$m and more especially from 0.1 to 10 $\mu$m.

Such layers may be prepared in a manner known per se, for example by dissolving the composition and, if desired, a homo- and/or co-polymer in a solvent, then casting to form a film and subsequently removing the solvent. After removal of the solvent the film can be released from the substrate and a free-standing membrane is obtained.

Other processes that may be used for the production of the membrane are those known from surface-coating technology, for example spin-coating, spraying or knife application processes. Spin-casting processes are preferred. The material according to the invention may also be obtained by injection-moulding or extrusion processes.

Suitable solvents include water, alcohols, ethers, esters, acid amides and ketones. Readily volatile solvents, especially tetrahydrofuran and halogenated hydrocarbons, or solvent mixtures, are especially suitable.

The layers may also be prepared by polymerisation on a support.

The invention accordingly relates also to a composition comprising (a) a compound of formula I alone or (b) together with at least one comonomer and, where appropriate, a solvent for components (a) and (b). For the compound of formula I, the comonomers, amounts thereof and solvents, the preferences indicated for embodiment A apply.

The membrane may be transparent or slightly opaque. It is preferably transparent. The layer is preferably hydrophilic.

The optical range in which the material as sensor can be excited extends from the ultraviolet range to the infrared range. The immobilised fluorophore-ionophores to be used in accordance with the invention have very suitable absorption and emission wavelength ranges that allow the use of known economically priced low-energy light sources, for example halogen or xenon lamps or light-emitting diodes. The preferred excitation source is a light-emitting diode having a wavelength of approximately 400 nm and above. The detectors used to detect the fluorescence may be, for example, photodiodes. Commercially obtainable optical fibres may be used in the excitation and detection. The sensor may therefore be changed after use on a patient.

The optical sensor is suitable especially for the quantitative determination of ions, especially cations, more especially metal cations, that are present in blood plasma, for example calcium, sodium or potassium cations, in an aqueous environment preferably using fluorescence spectrometry, measurements advantageously being taken in the region of the emission maxima. The determinations may be effected within short periods of time with a high degree of accuracy even in the case of low concentrations (for example extending from the molar range to the nanomolar range).

A very important advantage of the immobilised fluoroionophores is that they offer the possibility of carrying out measurements that are substantially independent of pH value. There is therefore a much freer choice of fluoroionophores since proton exchange at the fluorophore is not necessary for the detection of ions. In addition, direct measurement of the solution to be analysed is possible, which is of considerable commercial advantage. If desired, however, it is also possible in some cases for the measurements to be carried out in buffered analysis solutions when, for example, fluorophores are used that result in a signal change brought about by proton exchange.

The analyses may be carried out, for example, directly in body fluids (blood, urine, serum), natural waters or waste water, it being possible for cations that may interfere to be selectively bonded or removed beforehand. The composition according to the invention is suitable especially for determining in aqueous media physiological amounts of cations which, in the case of potassium, for example, may be approximately in the range from 0.5 to 20 mmol.

The ionophores are able to bind both cations and anions.

Cations are, for example, cations of metals from main groups I to V and sub-groups I to VIII of the Periodic Table of the Elements, the lanthanides and actinides. Examples of metals include Li, Na, K, Rb, Cs, Mg, Ca, Sr, Ba, B, Al, Ga, In, Tl, Sn, Pb, Sb, Bi, Cu, Ag, Au, Zn, Cd, Hg, Sc, Y, Ti, Zr, Hf, Cr, Mo, W, Mn, Fe, Co, Ni, Ru, Os, Rh, Ir, Pt, Pd, La, Ce, Pr, Nd, Pm, Sm, Eu, Gd, Tb, Dy, Ho, Er, Yb, Lu, Ac, Th, Pa, U, Np, Pu. Preferred cations are the alkali metal and alkaline earth metal ions, especially $Li^+$, $Na^+$, $K^+$, $Mg^{2+}$, $Ca^{2+}$ and $Sr^{2+}$, and more especially $K^+$, $Na^+$ and $Ca^{2+}$. Suitable ammonium cations are, for example, $NH_4^+$ and the cations of protonated primary, secondary and tertiary amines and of quaternary ammonium. The amines may contain from 1 to 40, especially from 1 to 20 and more especially from 1 to 12, carbon atoms. The quaternary ammonium may contain from 4 to 40, especially from 4 to 20, and more especially from 4 to 16, carbon atoms. Furthermore, organic ions, for example oligoalkylammonium ions, phosphonium ions, guanidine ions or choline ions, may be selectively bonded.

It is possible for anions that are derived from mineral acids, oxyacids and inorganic complex acids to be selectively bound. Examples are the halides and pseudohalides $F^-$, $Cl^-$, $Br^-$, $I^-$, $N_3^-$, $CN^-$, $OCN^-$ and $SCN^-$; anions of the inorganic oxyacids $NO_2^{2-}$, $NO_3^-$, $CO_3^{2-}$, $PO_4^{3-}$, $SO_4^{2-}$, $ClO_4^-$, $MnO_4^-$ and $ClO_3^-$; anions of the inorganic complex acids $Fe(CN)_6^{4-}$ and $Co(CN)_6^{3-}$; the anions of carboxylic acids, phenols; and nucleotide anions, such as adenosine phosphate.

Examples of neutral polar substances that may be selectively bound by the ionophore are urea, thiourea, guanine, guanidine, uric acid, choline, creatinine, amino acids and sugars; being lipophilic molecules, steroids, for example cholesterol, or lipids, for example triglycerides or lecithin, may be selectively bound.

In addition to the preferred fluorescence spectroscopy, other methods of optical measurement may also be used, for example surface plasmon resonance spectroscopy, absorption spectroscopy, reflection spectroscopy, interferometry or surface-enhanced Raman or fluorescence spectroscopy.

The invention relates also to a method for the optical determination of ions in aqueous test samples, in which method a sensor according to the invention is brought into contact with the said aqueous test sample and then the change in fluorescence of the fluorophore in the polymer layer is measured.

The method according to the invention may be carried out, for example, by fixing the support with the active polymer layer in an optical cell in which the active layer comes into contact with the test sample. The optical cell has a window through which the active layer can be irradiated for the purpose of excitation and through which the emitted fluorescence radiation can be measured using a spectrofluorometer. The wavelengths may be adjusted to provide maximum absorption for the irradiation and maximum emission for the fluorescence measurement. The intensity is measured as a function of time. The measuring system may be so arranged that the measurement is carried out discontinuously or continuously by, for example, pumping the test solution through the measuring cell. In order to determine unknown concentrations of cations, the system may first be calibrated using test samples of known concentration by plotting the concentrations against the intensity of the fluorescence.

If pH-dependent fluoroionophores are used, it is expedient to add pH buffers to the test sample since, on account of the pH dependency of the absorption spectrum and consequently also the fluorescence intensity of the fluorophore, the sensitivity of the measurement depends on the pH of the test solution. In another embodiment, however, the pH dependency may be determined and taken into account in the calculation. The pH range of the test sample may be, for example, from 4 to 8, preferably from 6.8 to 7.6. Suitable buffers are, for example, citrate buffers and phosphate buffers. Further buffer systems are described in U.S. Pat. No. 4,645,744, especially also those which are directly incorporated in the active layer so as to avoid addition to the test sample.

The invention relates also to the use of the optical sensor for the determination of cations or anions by fluorescence spectroscopy.

The following Examples illustrate the invention.

The following abbreviations are used in the Examples which follow:

h: hours
DMF: dimethylformamide
MS(FD): mass spectrometry (field desorption)
MS (FAB): mass spectrometry (fast atom bombardment)
THF; tetrahydrofuran
MS: mass spectrum
AIBN: α,α'-azoisobutyronitrile
RT: room temperature A) Synthesis of Precursors and Intermediates
A1) Linkage to Polymer and Core Structural Unit (Linker and Core)

EXAMPLE A1

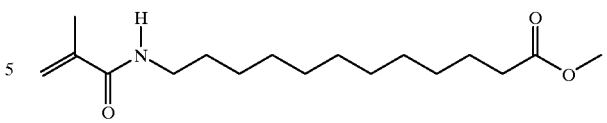

72 g (0.22 mol) of ω-aminododecanoic acid methyl ester hemidihydrosultate are suspended in 1 litre of $CH_2Cl_2$ and 70 ml (0.5 mol) of triethylamine are added thereto. The resulting solution is cooled to 5° C. and 24.1 ml (0.25 mol) of methacrylic acid chloride are added dropwise over the course of 20 min. An additional amount of triethylamine (6 ml) is added and the reaction mixture is stirred overnight at room temperature. 250 ml of water are added to the clear solution and the organic phase is removed. The aqueous phase is back-extracted with $CH_2Cl_2$ and the combined organic phases are washed with water, dried over $Na_2SO_4$ and concentrated by evaporation. The crude product is recrystallised from ethyl acetate/hexane. M.p. 48° C. Yield 86%. $^1$H-NMR($CDCl_3$): 5.78 (s, br., 1 H, NH); 5.66 (s, 1 H, HC=C); 5.30 (m, 1 H, HC=C); 3.66 (s, 3 H, $OCH_3$); 3.31 (q, J=7 Hz, N—$CH_2$); 2.30 (t, J=7 Hz, $CH_2CO$); 1.97 (m, 3 H, $CH_3$); 1.75–1.20 (m, 18 H, 9 $CH_2$).

EXAMPLE A2

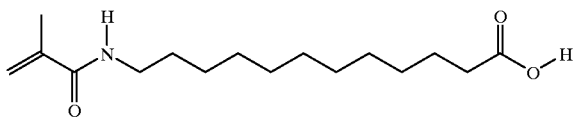

2.93 g (10 mmol) of methyl ester are heated for 4 hours at 60° C. with 100 ml of 4N HCl. The cold reaction mixture is extracted with ethyl acetate, dried over $Na_2SO_4$ and concentrated by evaporation, and the residue remaining is chromatographed on silica gel. Yield 3 g of white solids. $^1$H-NMR($CDCl_3$): 5.85 (s, br., 1 H, NH); 5.68 (s, 1 H, HC=C); 5.32 (m, 1 H, HC=C); 3.31 (q, J=7 Hz, N—$CH_2$); 2.35 (t, J=7 Hz, $CH_2CO$); 1.97 (m, 3 H, $CH_3$); 1.70–1.20 (m, 18 H, 9 $CH_2$).

EXAMPLE A3

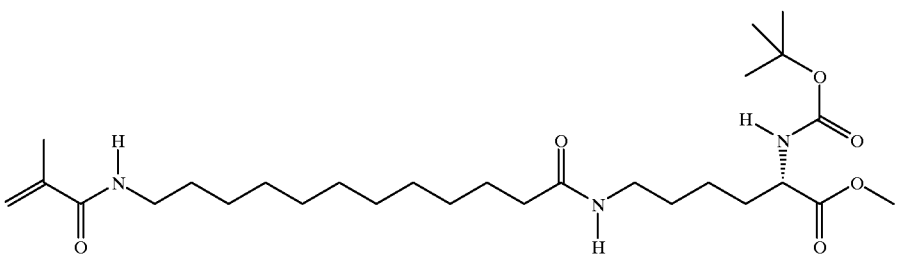

4.41 g (15.6 mmol) of carboxylic acid are dissolved in 90 ml of dry THF, and 2.66 g (1.05 eq.) of carbonyldiimidazole (CDl) are added thereto. The resulting clear solution is stirred for 2 h. A solution of 5 g (1 eq.) of BOC-lysine methyl ester acetate in 50 ml of dry THF is added. Subsequently, 6.53 ml (3 eq.) of triethylamine are added dropwise thereto, and the resulting mixture is stirred overnight and then poured into 200 ml of water. The aqueous phase is extracted with CH$_2$Cl$_2$, dried over Na$_2$SO$_4$ and concentrated by evaporation. Yield: 7.0 g (85%) of white crystals from ethyl acetate. M.p. 101° C.

$^1$H-NMR(CDCl$_3$): 5.84 (s, br., 1 H, NH); 5.68 (s, 1 H, HC=C); 5.64 (s, br., 1 H, NH); 5.3 (m, 1 H, HC=C); 5.10 (d, J=8, 1 H, NH); 4.27 (m, 1 H, CH); 3.75 (s, 3 H, OCH$_3$); 3.40–3.20 (m, 4 H); 2.18 (t, J=7 Hz, 2 H, CH$_2$CO); 1.97 (m, 3 H, CH$_3$); 1.90–1.15 (m, 33 H). MS: 525 (M$^+$).

EXAMPLE A4

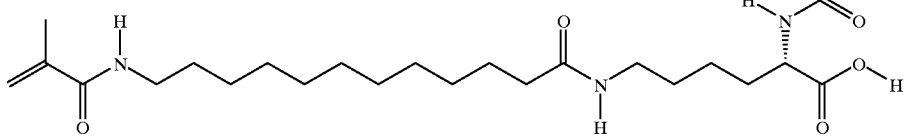

5.4 g (10 mmol) of methyl ester, 200 ml of MeOH, 200 ml of THF and 123.3 ml (12.33 mmol) of 0.1N NaOH are mixed at room temperature and stirred overnight. The reaction mixture is poured into 500 ml of CH$_2$Cl$_2$, and 15 ml of 1N HCl in 50 ml of water are added. The organic phase is removed, dried over Na$_2$SO$_4$ and concentrated by evaporation. The crude product is washed twice with 100 ml of ether and dried under a high vacuum. Yield 4.95 g (94 %). M.p. 103° C. $^1$H-NMR(CDCl$_3$): 6.00 (m, br., 2 H); 5.68 (s, 1 H, HC=C); 5.64 (s, br., 1 H, NH); 5.32 (m, 1 H, HC=C); 5.10 (d, J=8, 1 H, NH); 4.27 (m, 1 H, CH); 3.40–3.20 (m, 4 H); 2.18 (t, J=7 Hz, 2 H, CH$_2$CO); 1.97 (m, 3 H, CH$_3$); 1.90–1.15 (m, 33 H). MS: 511 (M$^+$).

EXAMPLE A5

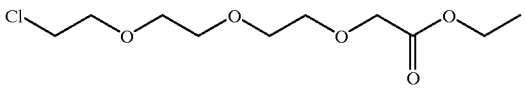

73 ml (0.5 mol) of triethylene glycol monochloride are dissolved in 400 ml of dry THF. 50 mg of rhodium acetate are added thereto. A solution of 105 ml (1 mol) of diazoacetic acid ethyl ester in 150 ml of dry THF is added dropwise over a period of 3 h. 50 mg portions of rhodium acetate are added every 30 min. An evolution of gas is observed throughout the entire period. The reaction mixture is stirred overnight, 50 ml of MeOH are then added and the mixture is concentrated by evaporation. The crude product is distilled at 0.08 mbar pressure. Boiling point of the pure product 118–124° C. Yield 57.9 g (45.5%).

$^1$H-NMR(CDCl$_3$): 4.23 (q, J=7, 3 H, CH$_3$); 4.16 (s, 2 H, CH$_2$); 3.80–3.60 (m, 12 H, 3 CH$_2$CH$_2$); 1.30 (t, J=7, 3 H, CH$_3$).

EXAMPLE A6

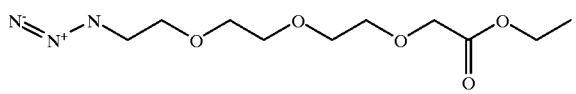

A mixture of 25.4 g (0.1 mol) of chloroethylene glycol ester and 9.75 g (0.15 mol) of sodium azide in 200 ml of DMF is heated at 105° C. for 6 h. The reaction mixture is diluted with 200 ml of diethyl ether, filtered and concentrated by evaporation. $^1$H-NMR(CDCl$_3$): 4.22 (q, J=7, 3 H, CH$_3$); 4.15 (s, 2 H, CH$_2$); 3.80–3.65 (m, 10 H, 2 CH$_2$CH$_2$; 1 CH$_2$); 3.38 (t, J=5, 2 H, CH$_2$); 1.28 (t, J=7, 3 H, CH$_3$).

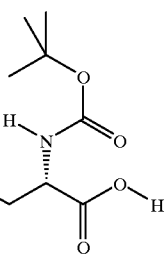

EXAMPLE A7

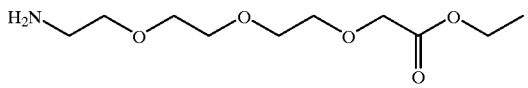

11 g (42 mmol) of azido ester are dissolved in 550 ml of absolute EtOH. After applying a vacuum and flushing the reaction flask with argon three times, 150 mg of PtO2 are added thereto. The application of a vacuum and introduction of gas are repeated, hydrogen being used as the gas. The reaction solution is stirred vigorously for 1.5 h, after which a further 150 mg of PtO$_2$ are added. After a further 1.5 h, the reaction mixture is filtered over Hyflo® and concentrated by evaporation. Yield 10.4 g of crude amino ester, which is immediately used in the next reaction step.

EXAMPLE A8

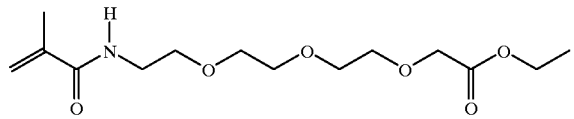

35.5 g (150 mmol) of amino ester and 18.5 ml (230 mmol) of pyridine are dissolved in 150 ml of CH$_2$Cl$_2$. 22.2 ml (230 mmol) of methacrylic acid chloride in 80 ml of CH$_2$Cl$_2$ are added dropwise in the course of 30 min. The reaction mixture is stirred overnight, washed three times with 100 ml portions of water, dried over Na$_2$SO$_4$ and concentrated by evaporation. The crude product is chromatographed on silica gel. Yield 30.1 g (66%). $^1$H-NMR (CDCl$_3$): 6.45 (s, br., 1 H, NH); 5.73 (s, br., 1 H, HC=C); 5.34 (m, 1 H, HC=C); 4.22 (q, J=7, 3 H, CH$_3$); 4.15 (s, 2 H, CH$_2$); 3.80–3.50 (m, 12 H, 3 CH$_2$CH$_2$); 1.96 (s, 3 H, CH$_3$); 1.30 (t, J=7.3 H, CH$_3$).

EXAMPLE A9

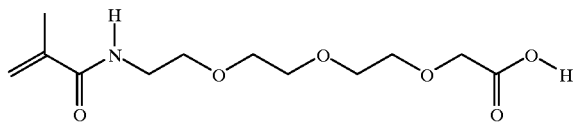

20 g (66 mmol) of ester are treated for 3 h at 60° C. with 120 ml of 4N HCl. 150 ml of water are added to the cooled mixture, and the mixture is saturated with NaCl and extracted with $CH_2Cl_2$. The organic phase is dried over $Na_2SO_4$ and concentrated by evaporation.

$^1$H-NMR(CDCl$_3$): 10.28 (s, br., 1 H, COOH); 6.61 (s, br., 1 H, NH); 5.75 (s, br., 1 H, HC=C); 5.35 (m, 1 H, HC=C); 4.16 (s, 2 H, CH$_2$); 3.80–3.50 (m, 12 H, 3 CH$_2$CH$_2$); 1.98 (s, 3 H, CH$_3$).

EXAMPLE A10

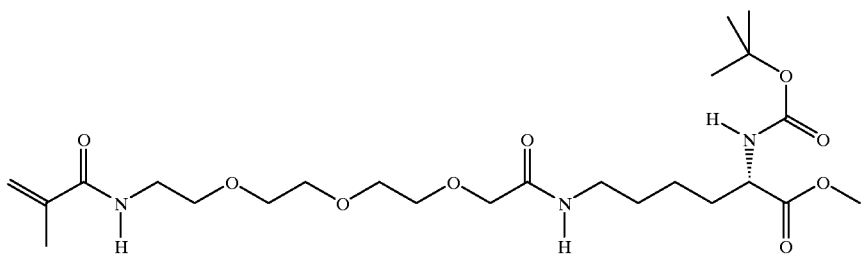

1.6 g (5.8 mmol) of carboxylic acid are dissolved in 10 ml of dry THF. 0.99 g (6.1 mmol) of CDI is added thereto; the evolution of $CO_2$ is observed. The resulting clear solution is stirred for 2 h. A solution of 1.85 g (5.8 mmol) of BOC-lysine methyl ester acetate in 15 ml of dry THF is added thereto. Subsequently, 2.42 ml (17.4 ml) of triethylamine are added dropwise and the resulting solution is stirred overnight and then poured into 200 ml of water. The aqueous phase is extracted with $CH_2Cl_2$ and the organic phase is washed with water, dried over $Na_2SO_4$ and evaporated to dryness. Yield 2.1 g (70% ). $^1$ H-NMR(CDCl$_3$): 6.97 (s, br., 1 H, NH); 6.50 (s, br., 1 H, NH); 5.71 (s, 1 H, HC=C); 5.35 (m, 1 H, HC=C); 5.2 (d, br., J=7, 1 H, NH); 4.35–4.20 (m, 1 H, CH); 4.00 (s, 2 H, OCH$_2$); 3.75 (s, 3 H, OCH$_3$); 3.72–3.48 (m, 12 H, 3 CH$_2$CH$_2$); 3.26 (q, J=7, 2 H, NCH$_2$); 1.99 (s, br., 3 H, CH$_3$); 1.95–1.30 (m, 6 H, 3 CH$_2$); 1.45 (s, 9 H, C(CH$_3$)$_3$).

2.1 g (4.06 mmol) of BOC-lysine methyl ester derivative and 48.7 ml (4.87 mmol) of 0.1N NaOH are mixed with 100 ml of THF and 100 ml of MeOH. The mixture is stirred for 18 h at room temperature, concentrated to approximately 50 ml and acidified with 15 ml of 0.5N HCl. The aqueous phase is extracted with $CH_2Cl_2$, and the organic phase is dried over $Na_2SO_4$ and concentrated using a rotary evaporator. Yield 1.89 g (93%). $^1$H-NMR(CDCl$_3$): 10.40 (s, br., 1 H, COOH); 6.97 (s, br., 1 H, NH); 6.50 (s, br., 1 H, NH); 5.71 (s, 1 H, HC=C); 5.35 (m, 1 H, HC=C); 5.2 (d, br., J=7, 1 H, NH); 4.35–4.20 (m, 1 H, CH); 4.00 (s, 2 H, OCH$_2$); 3.72–3.48 (m, 12 H, 3 CH$_2$CH$_2$); 3.26 (q, J=7, 2 H, NCH$_2$); 1.99 (s, br., 3 H, CH$_3$); 1.95–1.30 (m, 6 H, 3 CH$_2$); 1.45 (s, 9H, C(CH$_3$)$_3$).

EXAMPLE A11

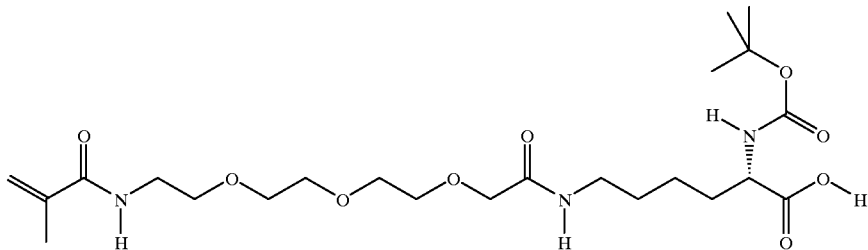

Synthesis of the Ionophores

EXAMPLE A12

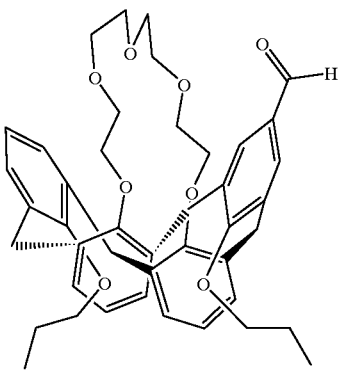

1.77 g (2.65 mmol) of 1,3-alternating di-n-propylcalix[4]crown-5 (*Chem. Europ. J.* 1996, 2, 436) are dissolved in 150 ml of $CH_2Cl_2$ and the solution is cooled to −15° C. under argon. 3.3 ml (14 eq.) of dichloromethyl methyl ether are added, followed by 4.37 ml (14 eq.) of fuming tin tetrachloride. The red mixture is stirred for 1 h and then poured into 100 ml of water, and the organic phase is removed and washed twice with water. The organic phase is dried over $Na_2SO_4$ and concentrated by evaporation. The residue is recrystallised from hexane/ethyl acetate 4:1. Yield 1.4 g (76%). M.p. 196° C. $^1$H-NMR($CDCl_3$): 9.92 (s, 1 H, CHO); 7.67 (s, 2 H, ar-H); IR(KBr): 1690 (CHO). MS: 733 $(M+K)^+$; 705 $(M+K-CO)^+$.

EXAMPLE A13

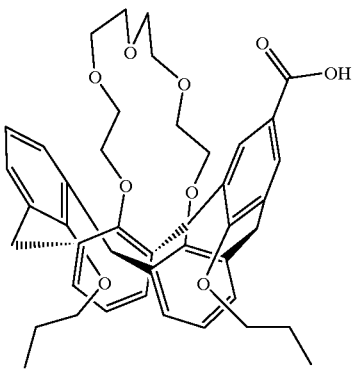

70 mg (0.1 mmol) of calixaldehyde, 0.045 ml (0.4 mmol) of 2-methyl-2-butene and a few drops of THF are dissolved in tert-BuOH. A mixture of 67.8 mg (0.6 mmol) of 80% $NaClO_2$ and 55.2 mg (0.4 mmol) of $NaH_2PO_4$ in 0.5 ml of water are added to that solution at room temperature. After stirring for 1 h, 10 ml of $CH_2Cl_2$ are added. A further 20 ml of $CH_2Cl_2$ and 10 ml of water are added and the organic phase is removed. It is dried over $Na_2SO_4$ and concentrated by evaporation, and the residue is chromatographed on silica gel. Yield 44 mg (62%) of white crystals having a melting point of 219° C. $^1$H-NMR($CDCl_3$): 7.89 (s, br. 2 H, ar-H); 0.67 (t, J=7.5, 3 H, $CH_3$); 0.63 (t, J=7.5, 3 H, $CH_3$). MS: 749 $(M+K)^+$; 733 $(M+Na)^+$; 710 $(M)^+$. Alternatively, the oxidation may be carried out also with $Bu_4N^+$ $KMnO_4^-$ in accordance with *J. Chem. Soc. Chem. Commun.*, 1978, 253.

Synthesis of the Fluorescent Dyes

EXAMPLE A14

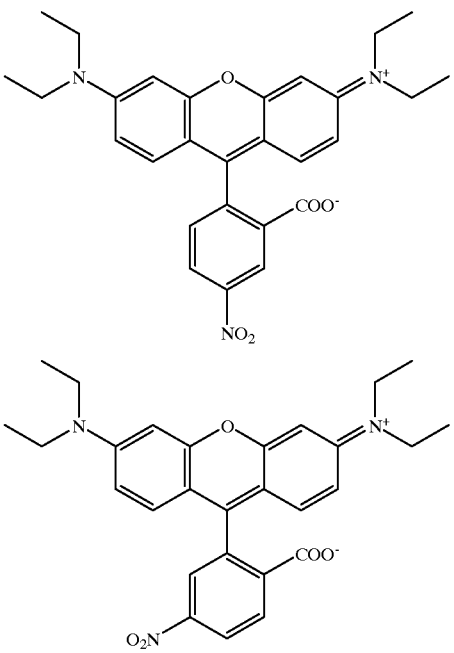

4.41 g (26.7 mmol) of 3-diethylaminophenol and 6 g (1.16 eq.) of 4-nitrophthalic acid anhydride are mixed with 30 ml of 1,2-dichlorobenzene and the mixture is heated at 190° C. for 5 hours. After removal of the solvent, the crude product is purified by chromatography on silica gel. Yield 4.25 g (64%) of an isomeric mixture.

EXAMPLE A15

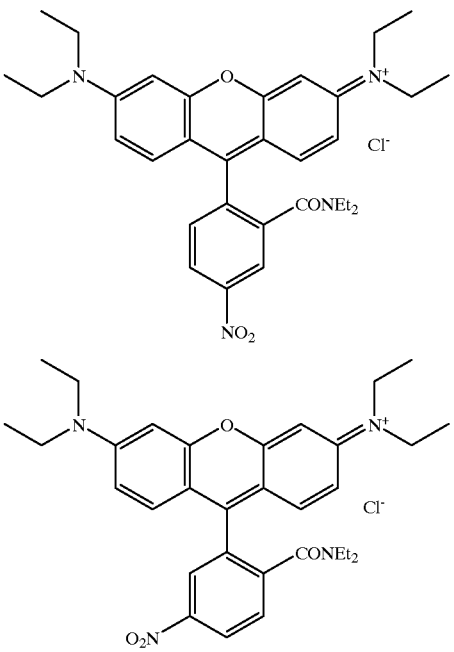

3.44 g (7.06 mmol) of the rhodamine isomers are dissolved in $CH_2Cl_2$. 8.95 g (10 eq.) of oxalyl chloride in 25 ml of $CH_2Cl_2$ are slowly added dropwise to that solution, accompanied by an intensive evolution of gas. After stirring for 2.5 h, the mixture is concentrated by evaporation and the residue is taken up in 20 ml of CH$_2$Cl$_2$. 1.55 ml (3 eq.) of diethylamine dissolved in 5 ml of CH$_2$Cl$_2$ are slowly added dropwise to that solution. After stirring overnight, the mixture is concentrated by evaporation, taken up in CH$_2$Cl$_2$, washed with 2N HCl and dried over Na$_2$SO$_4$. The purification is carried out by chromatography on silica gel. Yield 2.62 g (68%) of a 1:1 isomeric mixture. MS(FD): 543 (M)$^+$.

EXAMPLE A16

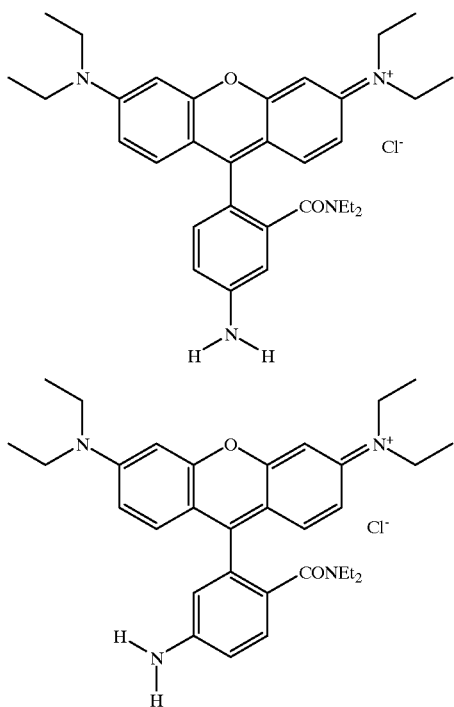

3.0 g (5.51 mmol) of nitrorhodamine isomeric mixture, 180 mg of activated carbon/FeCl$_3$.6H$_2$O catalyst and 0.35 ml (10 eq.) of asymmetrical dimethyl hydrazine are mixed with 60 ml of MeOH and the mixture is stirred at 80° C. for 13 h. The solvent is removed and the residue is purified by chromatography on silica gel. Yield 2.48 g (88%) of dark solids. MS(FAB): 513 (M+H)$^+$.

EXAMPLE A17

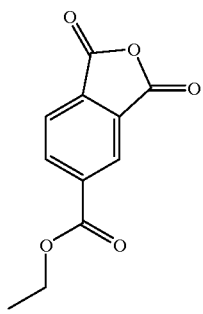

50 g of benzene-1,2,4-tricarboxylic acid 1,2-anhydride-4-chloride are dissolved in 800 ml of CH$_2$Cl$_2$ and the solution is cooled to 0° C. A solution of 10.94 g (1 eq.) of ethanol and 25.45 g of 2,6-lutidine in 200 ml of CH$_2$Cl$_2$ is added dropwise thereto. After stirring for 1.5 h at 0° C. and for 1.5 h at room temperature, the mixture is evaporated to dryness. The crystalline residue is stirred in ethyl acetate for 1 h, filtered, and the filtrate is concentrated by evaporation: 52 g (99%) of light-yellow crystals. M.p. 98–100° C. MS(FD): 220 (100%).

EXAMPLE A18

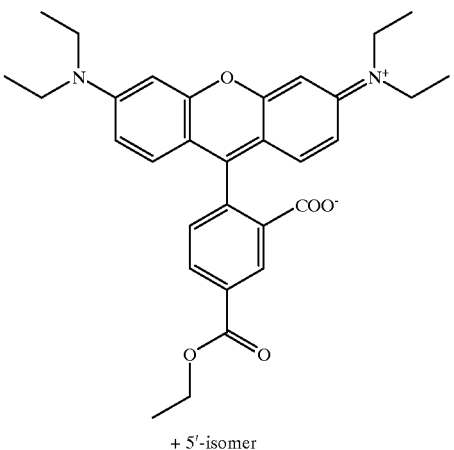

+ 5'-isomer 7.76 g of 3-diethylaminophenol and 12.0 g (1.16 eq.) of benzene-1,2,4-tricarboxylic acid 1,2-anhydride-4-ethyl ester are dissolved in 60 ml of 1,2-dichlorobenzene and the solution is heated at 190° C. for 5.5 h, with subsequent removal of the solvent by distillation in vacuo. The isomeric mixture is separated by chromatography on silica gel, a total yield of 58% being obtained. Isomer A $^1$H-NMR(DMSO-d$_6$): 8.4 (s, 1 H); 8.29 (d, J=8 Hz, 1 H); 7.40 (d, J=8 Hz, 1 H); 6.55–6.35 (m, 6 H); 4.4 (q, J=7 Hz, 2H); 3.4–3.3 (m, 8 H); 1.35 (t, J=7 Hz, 3 H); 1.15–1.0 (m, 12 H). Isomer B $^1$H-NMR(DMSO-d$_6$): 8.38 (d, J=8 Hz, 1 H); 8.26 (d, J=8 Hz, 1 H); 7.8 (s, 1 H); 6.7–6.5 (m, 6 H); 4.4 (q, J=7 Hz, 2 H); 3.55–3.45 (m, 8 H); 1.4 (t, J=7 Hz, 3 H); 1.3–1.15 (m, 12 H).

EXAMPLE A19

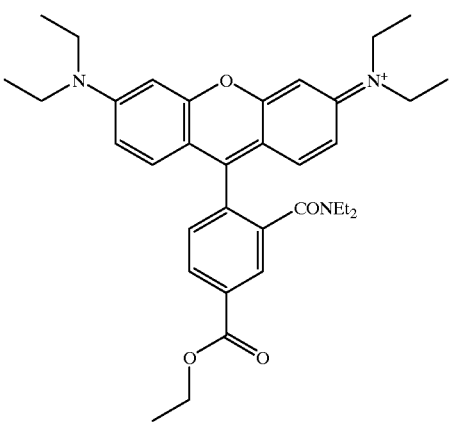

16.7 g of rhodaminecarboxylic acid are dissolved in 300 ml of CH$_2$Cl$_2$, and a solution of 20.6 g (5 eq.) of oxalyl chloride in CH$_2$Cl$_2$ is slowly added dropwise thereto. After stirring for 2 h at room temperature, the mixture is evaporated to dryness. The acid chloride is taken up in 250 ml of CH$_2$Cl$_2$, and a solution of 7.12 g (2 eq.) of diethylamine in 50 ml of CH$_2$Cl$_2$ is added. After stirring overnight, the reaction mixture is washed with 2N HCl. The aqueous phase is back-extracted with $CH_2Cl_2$. The combined organic phases are dried over $Na_2SO_4$ and concentrated by evaporation, and the residue is chromatographed on silica gel. Yield 19.33 g (99%). $^1$H-NMR(CDCl$_3$): 8.3 (dd, J=8 Hz, J=2 Hz, 1 H); 8.2 (d, J=2 Hz, 1 H); 7.47 (d, J=8 Hz, 1 H); 7.2 (d, J=10 Hz, 2 H); 7.05 (dd, J=10 Hz, J=2 Hz, 2 H); 6.8 (d, J=2 Hz, 2 H); 4.45 (q, J=7 Hz, 2 H); 3.7–3.6 (m, 8 H); 3.25–3.15 (m, 4 H); 1.45 (t, J=7 Hz, 3 H); 1.35 (t, J=7 Hz, 12 H); 1.15 (t, J=7 Hz, 3 H); 0.66 (t, J=7 Hz, 3 H).

EXAMPLE A20

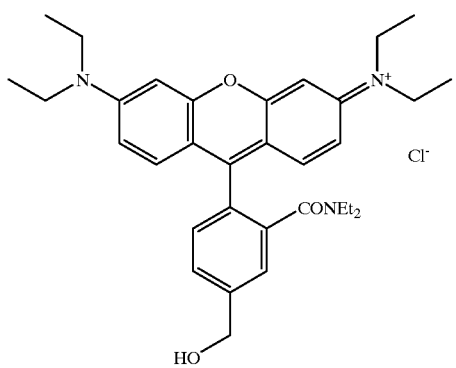

19.3 g of rhodamine amide dissolved in 200 ml of $CH_2Cl_2$ are slowly added dropwise to a suspension of 2.66 g (2.2 eq.) of LiAlH$_4$ in THF while cooling with ice. After stirring for 2.5 h, 100 ml of 2N HCl are added dropwise, followed by 150 ml 2N NaOH. The aqueous phase is repeatedly extracted with ethyl acetate, and the combined organic phases are dried over $Na_2SO_4$ and concentrated by evaporation. The slightly pink-coloured residue is purified by chromatography. The pure intermediate (reduced rhodamine, leukoform) is dissolved in 250 ml of $CH_2Cl_2$, and 2.87 g (1 eq.) of DDQ (2,3-dichloro-5,6-dicyano-1,4-benzoquinone) are added thereto. An additional 1.43 g and 0.6 g of DDQ are added after 1 and 2 h respectively. The reaction solution is diluted with $CH_2Cl_2$ and washed in succession with 2N NaOH, 2N HCl and brine. Drying, concentration by evaporation and purification by chromatography on silica gel yield 9.7 g (54%) of pure hydroxymethylrhodamine amide.

$^1$H-NMR(CDCl$_3$): 7.85 (dd, J=8 Hz, J=2 Hz, 1 H); 7.6 (d, J=2 Hz, 1 H); 7.34 (d, J=10 Hz, 2 H); 7.28 (d, J=8Hz, 1 H); 6.88 (dd, J=10 Hz, J=2 Hz, 2 H); 6.73 (d, J=2 Hz, 2 H); 5.77 (t, J=7 Hz, 1 H); 4.94 (d, J=7 Hz, 2 H); 3.7–3.55 (m, 8 H); 3.3–3.3–3.15 (m, 4 H); 1.4–1.25 (m, 12 H); 1.13 (t, J=7 Hz, 3 H); 0.66 (t, J=7 Hz, 3 H).

EXAMPLE A21

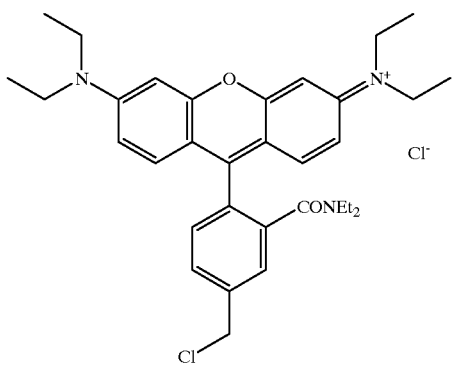

2.0 g of hydroxymethylrhodamine amide and 0.9 g of Et$_3$N (2.5 eq.) are dissolved in 30 ml of $CH_2Cl_2$ and, at 0° C., a solution of 0.61 g (1.5 eq.) of methanesulfonyl chloride in 10 ml of $CH_2Cl_2$ is added dropwise thereto. After stirring overnight, the mixture is diluted with $CH_2Cl_2$ and extracted with 2N HCl. The organic phase is dried over $Na_2SO_4$ and purified by chromatography on silica get. Yield 2.5 g (99%) of dark-violet crystals. $^1$H-NMR(CDCl$_3$): 7.7 (dd, J=8 Hz, J=2 Hz, 1 H); 7.58 (d, J=2 Hz, 1 H); 7.39 (d, J=8 Hz, 1 H); 7.26 (d, J=10 Hz, 2 H); 7.03 (dd, J=10 Hz, J=2 Hz, 2 H); 6.77 (d, J=2 Hz, 2 H); 4.76 (d, J=7Hz, 2 H); 3.7–3.55 (m, 8 H); 3.3–3.15 (m, 4 H); 1.4–1.25 (m, 12 H); 1.13 (t, J=7 Hz, 3 H); 0.66 (t, J=7 Hz, 3 H).

EXAMPLE A22

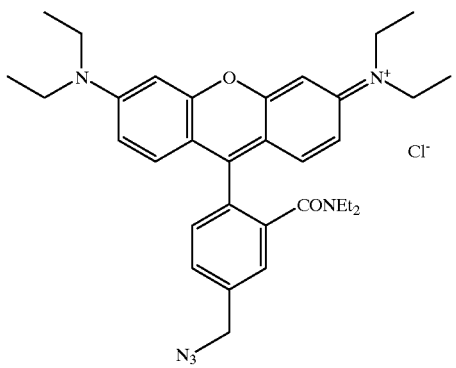

4.4 g of chloromethylrhodamine and 2.95 g of sodium azide are dissolved in 75 ml of DMSO and the solution is heated at 50° C. for 4.75 h. The reaction solution is taken up in $CH_2Cl_2$ and washed twice with 2N HCl. The organic phase is dried over $Na_2SO_4$ and concentrated by evaporation and the residue is chromatographed on silica gel. Yield quantitative.

$^1$H-NMR(CDCl$_3$): 7.65 (dd, J=8 Hz, J=2 Hz, 1 H); 7.5 (d, J=2 Hz, 1 H); 7.41 (d, J=8 Hz, 1 H); 7.26 (d, J=10 Hz, 2 H); 7.01 (dd, J=10 Hz, J=2 Hz, 2 H); 6.78 (d, J=2 Hz, 2 H); 4.6 (d, J=7 Hz, 2 H); 3.7–3.5 (m, 8 H); 3.25–3.1 (m, 4 H); 1.4–1.25 (m, 12 H); 1.13 (t, J=7 Hz, 3 H); 0.66 (t, J=7 Hz, 3 H).

EXAMPLE A23

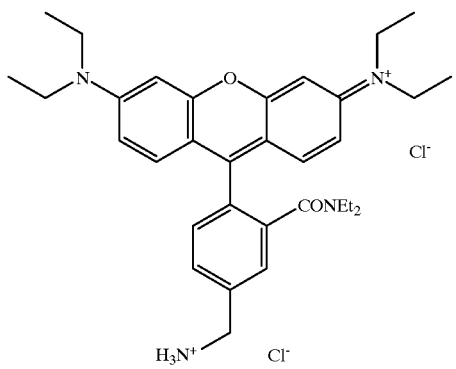

2.3 g of azidomethylrhodamine and 1.38 g (1.5 eq.) of triphenylphosphine are stirred for 2 h in pyridine. The intermediate adduct is decomposed with 60 ml of 25% ammonia at room temperature for 4 h. After concentration by evaporation, the residue is taken up in 2N HCl and extracted with $CH_2Cl_2$. The organic phase is discarded, and the aqueous phase is adjusted to pH 12 and extracted with $CH_2Cl_2$. The organic phase is dried over $Na_2SO_4$ and, after filtration, treated with $HCl_{gas}$/dioxane. After concentration by evaporation, the residue is purified by chromatography on silica gel. Yield of aminomethylrhodamine dichloride 1.45 g (66%). $^1$H-NMR($CDCl_3$): 8.04 (dd, J=8 Hz, J=2 Hz, 1 H); 7.78 (d, J=2 Hz, 1 H); 7.4 (2 d superimposed, J=8 Hz, 3 H); 7.02 (dd, J 10 Hz, J=2 Hz, 2 H); 6.7. (d, J=2 Hz, 2 H); 4.33 (d, J=7 Hz, 2 H); 3.7–3.5 (m, 8 H); 3.4–3.1 (m,4 H); 1.4–1.25 (m, 12 H); 1.13 (t, J=7 Hz, 3 H); 0.6 (t, J=7 Hz, 3 H).

EXAMPLE A24

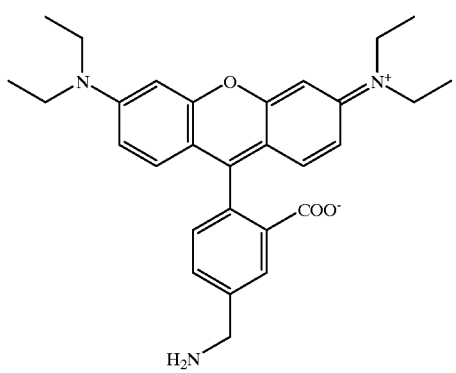

990 mg of aminomethylrhodamine dichloride are dissolved in 20 ml of 5N sulfuric acid and the solution is stirred at 120° C. for 30 h. The reaction mixture is poured into 2N NaOH (pH>10). The aqueous phase is extracted with $CH_2Cl_2$, the organic phase is dried over $Na_2SO_4$ and the residue is purified by chromatography. Yield 665 mg (80%) of amino-methylrhodaminecarboxylic acid. $^1$H-NMR ($CDCl_3$): 7.93 (d, J=2 Hz, 1 H); 7.6 (dd, J=8 Hz, J=2 Hz, 1 H); 7.17 (d, J=8 Hz, 3 H); 6.56 (d, J=10 Hz, 2 H); 6.43 (d, J=2 Hz, 2 H); 6.31 (dd, J=10 Hz, J=2 Hz, 2 H); 4.04 (d, J=7 Hz, 2 H); 3.35 (q, J=7 Hz, 8 H); 1.16 (t, J=7 Hz, 12 H).

EXAMPLE A25

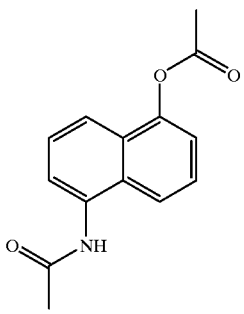

45 g of 5-amino-1-naphthol are dissolved in 500 ml of pyridine and the solution is cooled to 0° C. 54 ml (2 eq.) of acetic anhydride are added dropwise over a period of 30 min. After being stirred for 3.5 h at room temperature, the reaction mixture is concentrated by evaporation and taken up in 1 litre of 2N HCl. The precipitate is filtered off and dried in vacuo. The dried residue is extracted with ethyl acetate in a Soxhlet extractor. The solvent is removed and the residue is taken up in ethanol, activated carbon is added and the mixture is refluxed. After hot filtration the mixture is cooled, the product crystallising out. Yield 67%, brown solids. $^1$H-NMR(DMSO-$d_6$): 10.02 (s, br., 1 H); 8.01 (d, J=8 Hz, 1 H); 7.8–7.7 (m,2 H); 7.6–7.5 (m, 2 H); 7.34 (d, J=8 Hz, 1 H); 2.47 (s, 3 H); 2.2 (s, 3 H).

EXAMPLE A26

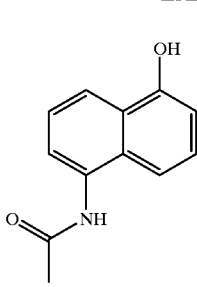

45.8 g of diacetate are dissolved in 200 ml of methanol, and 260 ml of 0.8N tetrabutyl-ammonium hydroxide in methanol are added thereto. After stirring overnight, the methanol is removed by distillation and the residue is taken up in 2N HCl and extracted with ethyl acetate. The organic phase is dried over $Na_2SO_4$ and concentrated by evaporation, and the residue is chromatographed on silica gel. Yield 24 g (63%). $^1$H-NMR(DMSO-$d_6$): 10.19 (s, br., 1 H); 9.82 (s, br., 1 H); 7.99 (d, J=8 Hz, 1 H); 7.67 (d, J=8 Hz); 7.52 (d, J=8 Hz, 1 H); 7.4 (t, J=8 Hz); 7.34 (t, J=8 Hz, 1 H); 6.9 (d, J=8 Hz, 1 H); 2.18 (s, 3 H).

EXAMPLE A27

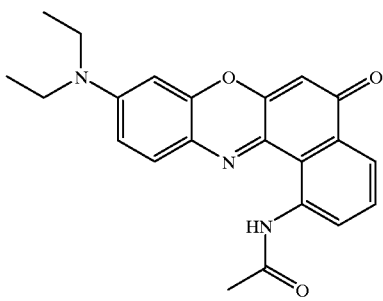

15 g of 5-dimethylamino-2-nitrosophenol, 15.5 g of 5-N-acetylamino-1-naphthol and 1.03 g of $AlCl_3$ are mixed into 350 ml of 1,2-dichlorobenzene and the mixture is heated at 140° C. for 67 h. The solvent is removed by distillation and the residue is taken up in $CH_2Cl_2$ and MeOH and filtered over Hyflo®. The filtrate is concentrated by evaporation and the residue is purified by chromatography. Yield 14%. $^1$H-NMR($CDCl_3$): 13.43 (s, br., 1 H); 9.03 (dd, J=1 Hz, J=9 Hz, 1 H); 8.06 (dd, J=1 Hz, J=9 Hz, 1 H); 7.58 (t, J=9 Hz, 1 H); 7.35 (d, J=10 Hz, 1 H); 6.61 (dd, J=10 Hz, J=2 Hz, 1 H); 6.41 (d, J=2 Hz, 1 H); 3.47 (q, J=7 Hz, 4 H); 1.27 (t, J=7 Hz, 6 H).

EXAMPLE A28

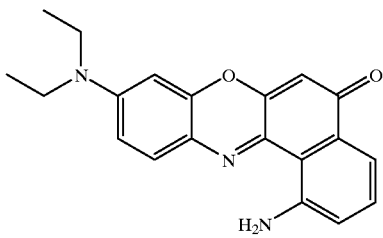

250 mg of acetylated dye are dissolved in 5 ml of $AcOH/H_2SO_4$ (5:2) and the solution is heated at 60° C. for 4.5 h. The reaction solution is poured into 2N NaOH (pH 11–12) while cooling with ice. The organic phase is washed with water, dried over $Na_2SO_4$ and concentrated by evaporation and the residue is chromatographed on silica gel. Yield 85%, violet crystals. $^1$H-NMR($CDCl_3$): 7.71 (dd, J=1 Hz, J=9 Hz, 1 H); 7.45 (dd, J=1 Hz, J=9 Hz, 1 H); 7.38 (t, J=9 Hz, 1 H); 7.0 (s, br., 2 H); 6.95 (d, J=10 Hz, 1 H); 6.59 (dd, J=10 Hz, J=2 Hz, 1 H); 6.42 (d, J=2 Hz, 1 H); 3.43 (q, J=7 Hz, 4 H); 1.25 (t, J=7 Hz, 6 H).

EXAMPLE A29

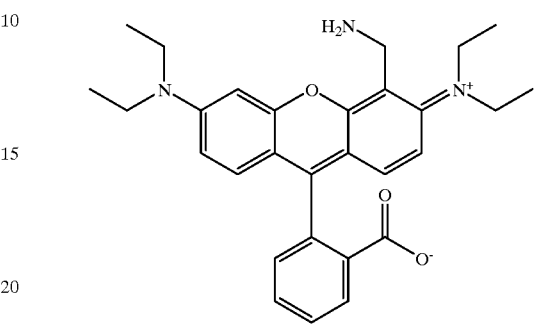

5.7 g (40 mmol) of boron trifluoride ethyl etherate are added to a solution of 4.8 g (10 mmol) of rhodamine B (hydrochloride, E. Merck, Darmstadt) and 1.1 g (12 mmol) of acetamidomethanol in 250 ml of dichloroethane. The mixture is heated at 80° C. for 3 h and the reaction mixture, cooled to room temperature, is poured onto ice and extracted with methylene chloride. 4'-(Acetamidomethyl)-N,N,N',N'-tetraethylrhodamine is obtained as intermediate. The organic phases are dried over sodium sulphate and fully concentrated, yielding 5.6 g of product which is taken up in 400 ml of 4N hydrochloric acid and heated at 100° C. for 2 h. At room temperature, the mixture is rendered neutral with 2N sodium hydroxide solution and extracted with methylene chloride. The organic phases are dried over sodium sulfate and fully concentrated. The residue is chromatographed on silica gel (eluant: methylene chloride/methanol 20:1), yielding 2.5 g of title compound in a yield of 53%. $^1$H-NMR ($CDCl_3$): 8.0 (d, 1 H); 7.65 (t, 1 H); 7.6 (t, 1 H); 7.25 (d, 1 H); 6.8 (d, 1 H); 6.6 (d, 1 H); 6.55 (d, 1 H); 6.5 (d, 1 H); 6.35 (dd, 1 H); 4.35 (d, 1 H); 4.3 (d, 1 H);3.75 (br, 1 ); 3.35 (q, 4 H); 3.0 (q, 4 H); 1.2 (t, 6 H); 1.0 (t, 6 H). MS $FAB^+$: 472 (M+1), $FAB^-$: 471 (M).

B) Synthesis of the Fluoroionophores

EXAMPLE B1

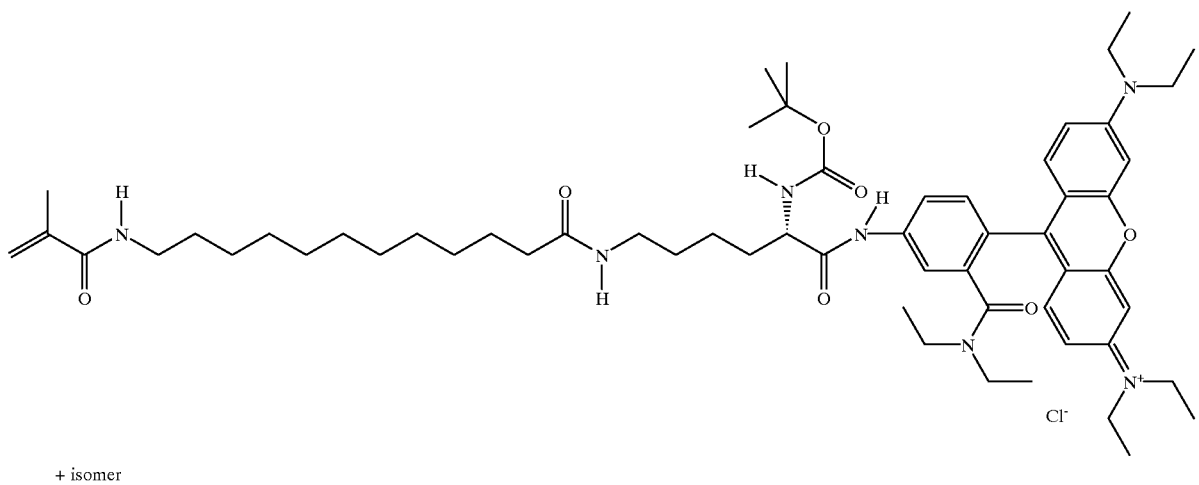

+ isomer 511 mg (1 mmol) of the carboxylic acid from Example A4 are dissolved in 5 ml of $CH_2Cl_2$, and 178 mg (1.1 eq.) of CDI are added. After 2 h, a solution of 513 mg (1 mmol) of 4-aminorhodamine/5-amino-rhodamine (Example 16) in 25 ml of $CH_2Cl_2$ is added dropwise and the mixture is stirred for 20 h. The reaction mixture is concentrated by evaporation and chromatographed on silica gel. Yield 280 mg (28%) of violet solids. MS: 1005 ($M^+$).

EXAMPLE B2

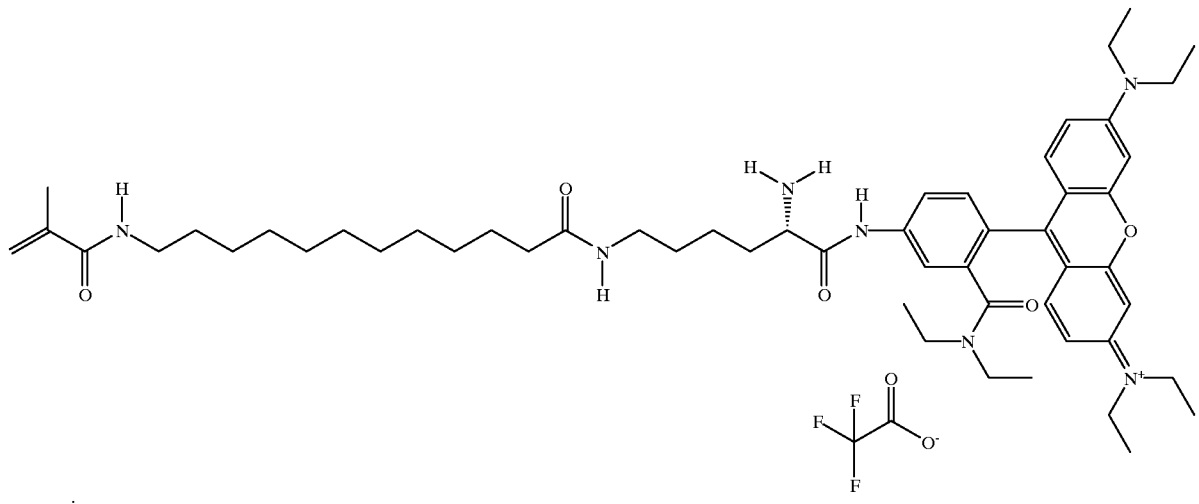

+ isomer 280 mg (0.278 mmol) of BOC-protected lysine derivative are dissolved in 2.5 ml of $CH_2Cl_2$ and 2.5 ml of trifluoroacetic acid. The mixture is stirred for 20 min. in the dark and then concentrated to dryness by evaporation. The residue is chromatographed on silica gel with $CH_2Cl_2$/MeOH 95:5. Yield 210 mg (74%). MS: 906 ($M^+$).

EXAMPLE B3

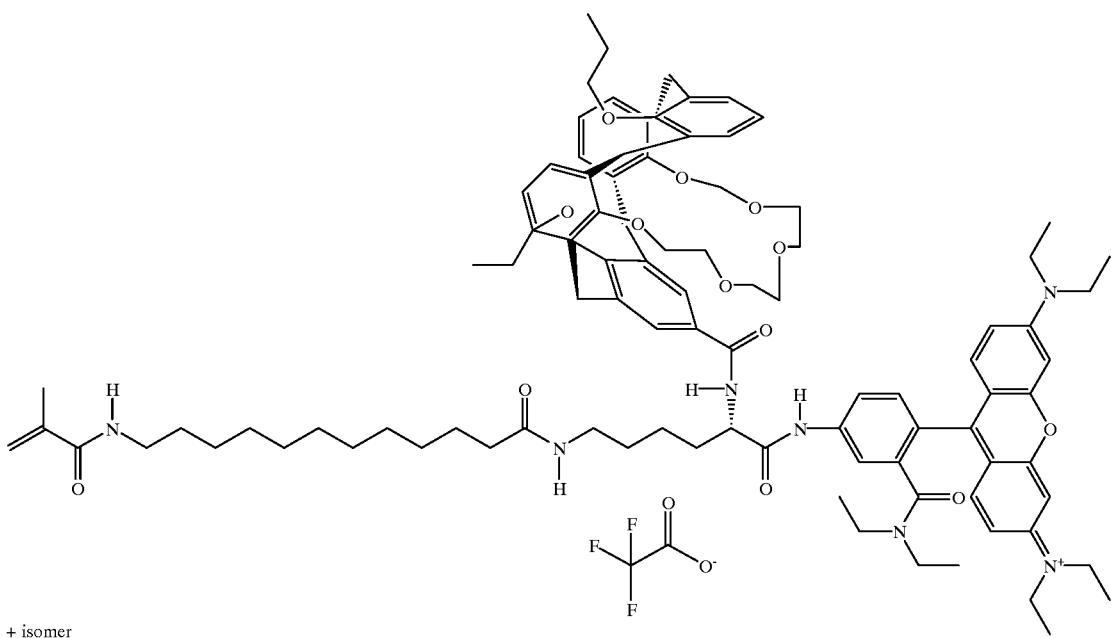

+ isomer 50 mg (0.07 mmol) of 1,3-alternating di-n-propylcalix[4]crown-5-carboxylic acid (Example A13) are dissolved in 3 ml of dry $CH_2Cl_2$ and then 0.5 ml of oxalyl chloride is added. After 30 min., the reaction mixture is concentrated by evaporation and dissolved in 2 ml of dry $CH_2Cl_2$. The solution is added to a mixture of 71.8 mg (0.07 mmol) of lysine derivative from Example 31, 25 mg (3.5 eq.) of triethylamine and 2 drops of DMF in 2 ml of $CH_2Cl_2$. Stirring overnight, concentration by evaporation and chromatography on silica yield 61 mg (54%) of the desired product. MS: 1598 ($M^+$).

EXAMPLE B4

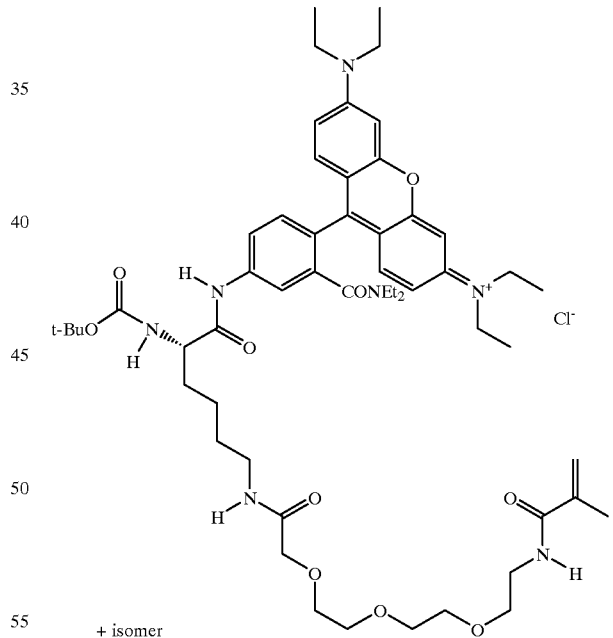

+ isomer 503 mg (1 mmol) of the carboxylic acid from Example A4 are dissolved in 5 ml of $CH_2Cl_2$, and 178 mg (1.1 eq.) of CDI are added thereto. After 2 h, a solution of 513 mg (1 mmol) of 4-amino-rhodamine/5-amino-rhodamine (Example 16) in 25 ml of $CH_2Cl_2$ is added dropwise. The reaction mixture is stirred for 20 h and concentrated by evaporation, and the residue is chromatographed on silica gel. Yield 110 mg (11%) of violet solids.

EXAMPLE B4
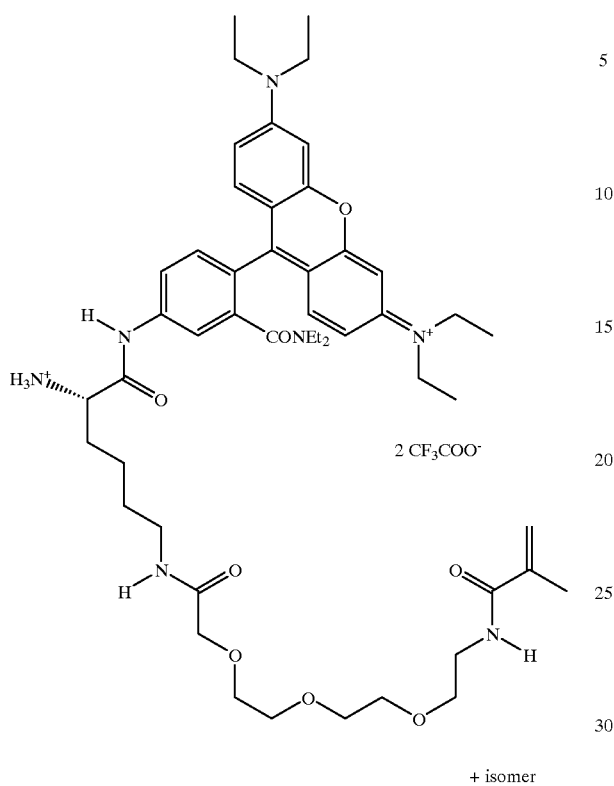
+ isomer
110 mg (0.106 mmol) of BOC-protected compound are dissolved in $CH_2Cl_2/CF_3COOH$ (5:1) (5 ml) at room temperature and the solution is stirred for 3 h. The reaction solution is concentrated by evaporation and the residue is chromatographed on silica gel ($CH_2Cl_2$/MeOH 9:1). Yield 70 mg (65%). MS(FAB): 898 $(M+H)^+$.
EXAMPLE B5
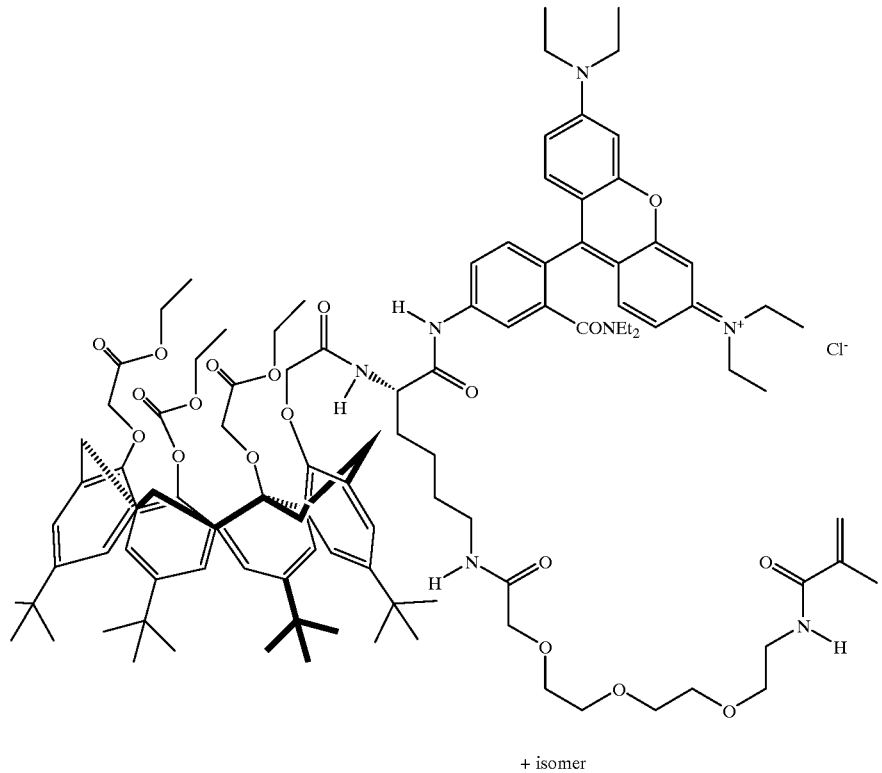
+ isomer 95 mg (0.099 mmol) of calixarene-triester-monocarboxylic acid (*J. Chem. Soc., Perkin Trans* 1 1990, 431; ibid., 1992, 1595) are dissolved in 0.5 ml of $SOCl_2$ and the solution is heated at 80° C. for 10 min. After concentration by evaporation, the residue is taken up in $CH_2Cl_2$ and added dropwise to a solution of 50 mg (0.0495 mol) of lysine dye derivative (Example A34) and 35 mg (0.35 mmol) of triethylamine in $CH_2Cl_2$. After 16 h, the reaction solution is diluted with $CH_2Cl_2$ and washed with 2N HCl. Concentration by evaporation after drying and purification by chromatography yield 55 mg (60%) of violet solids. MS(FAB): 1844 (M+H)$^+$.

EXAMPLE B6

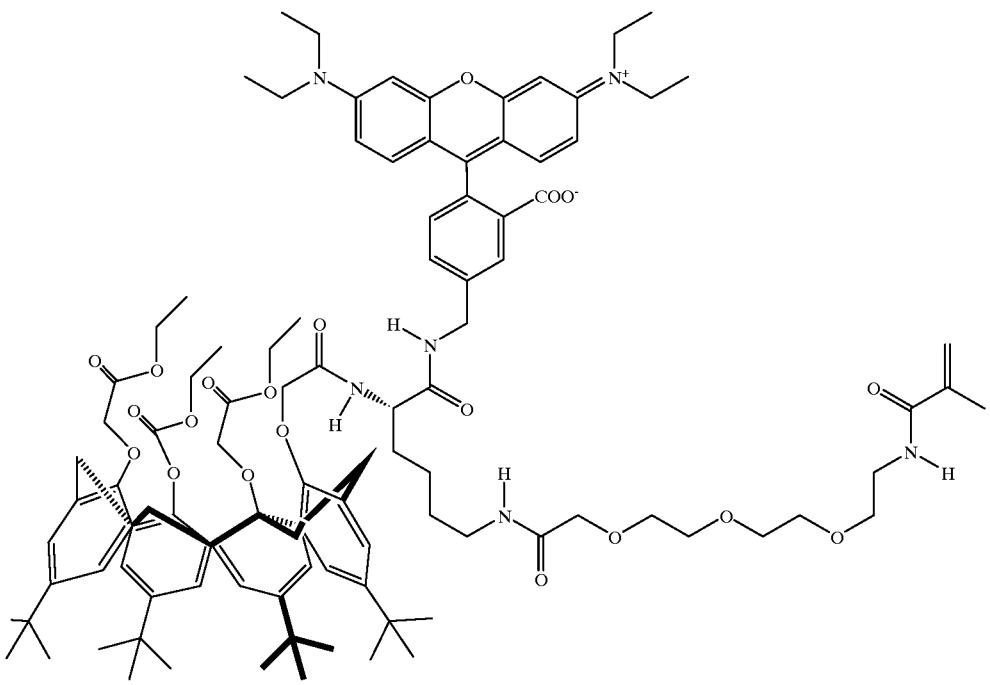

The above compound is prepared analogously to the syntheses described hereinbefore. MS(FAB): 1825 (M+Na)$^+$. Selected characteristic signals in $^1$H-NMR (CDCl$_3$): 5.81 (s, br., 1 H, CH), 5.26 (s, br., 1 H, CH); 1.87 (s, br., 3 H, CH$_3$); 1.43–1.33 and 1.33–1.20 (m, 7 CH$_3$); 1.15 (s, 36 H, 4 t-Bu).

C) Preparation of Polymers

EXAMPLE C1

Preparation of a Matrix Polymer for Non-covalently Immobilised Fluorophores Example C1.1

1.75 g (17.64 mmol) of N,N-dimethylacrylamide (DMAA), 3.25 g (17.64 mmol) of 2-ethyl hexyl acrylate (EHA) and 25 mg of AIBN are dissolved in 15 ml of dioxane in a flask. The flask is closed by a three-way tap and, by introducing nitrogen and subsequently freezing, applying a vacuum and thawing, a nitrogen atmosphere is produced in the flask. The batch is polymerised at 60° C. for 96 hours. The viscous mass is diluted with 5 ml of dioxane and the polymer is precipitated in 1.5 litres of deionised water. The polymer is filtered off, dried for 24 hours at 40° C. under a slight vacuum, dissolved in 10 ml of dioxane and re-precipitated in 1.5 litres of deionised water, filtered and dried under a high vacuum.

Yield: 4.8 g (96%), inherent viscosity ηinh of a 5% solution in dioxane at 25° C. is 0.37 dl/g, glass transition temperature $T_g$=−12.0° C., content of DMAA in the polymer 47.4 mol % (from elemental analysis).

EXAMPLE C1.2

2.70 g (15.95 mmol) of diacetone acrylamide (DAAA), 2.30 g (15.95 mmol) of hydroxybutylacrylate (HOBA) and 25 mg of AIBN are dissolved in 45 ml of DMSO. The further preparation is carried out analogously to Example C1.1, the polymerisation being carried out at 60° C.

Yield: 4.23 g (84%), ηinh=0.46 dl/g (0.5% solution in methanol at 25° C.), Tg=37.2° C., content of DAAA in the polymer: 47.5 mol % (from elemental analysis).

EXAMPLE C1.3

Prepared analogously to Example C1.2 using 75% DAAA and 25% HOBA; yield: 74% ηinh=0.40 dl/g (0.5% solution in methanol at 25° C.), Tg=69.8° C., content of DAAA in the polymer: 70.5 mol % (from elemental analysis).

EXAMPLE C1

Preparation of a Matrix Polymer for Covalently Immobilised Fluorophores

EXAMPLE C2.1

2.16 g (12.76 mmol) of DAAA, 1.84 g (12.76 mmol) of HOBA, 20 mg of AIBN and 20 mg of B3 are dissolved in 36 ml of DMSO. The sample is prepared, polymerised and worked up as in Example C1.2.

Yield: 3.7 g (92.5%), ηinh=0.47 dl/g (0.5% solution in methanol at 25° C.), Tg=35.5° C. content of DAAA in the polymer: 47.5 mol % (from elemental analysis).

EXAMPLE C2.2

1.4 g (14.11 mmol) of DMAA, 2.60 g (14.11 mmol) of EHA, 20 mg of AIBN and 20 mg of B3 are dissolved in 36 ml of DMSO and the solution is prepared for polymerisation in the manner described in Example C2.1. The duration of the polymerisation is 96 hours at 60° C.

Yield: 3.4 g (85%), ηinh=0.795 dl/g (0.5% THF solution at 25° C.), Tg=24.1° C., the polymer contains 46.3 mol % DMAA (calculated from elemental analysis).

EXAMPLE C2.3

2.16 g (12.76 mmol) of DAAA, 1.84 g (12.76 mmol) of HOBA, 20 mg of AlBN and 18.5 mg of B5 are dissolved in 36 ml of DMSO, and the sample is prepared, polymerised and worked up in the manner described in Example C2.1.

Yield: 3.47 g (87%), ηinh=0.386 dl/g (0.5% solution in methanol at 25° C.), Tg=35.6° C., content of DAM in the polymer: 45.8 mol % (calculated from elemental analysis).

EXAMPLE C2.4

1.40 g (14.11 mmol) of DMAA, 2.60 g (14.11 mmol) of EHA, 20 mg of AlBN and 18.5 mg of B5 are dissolved in 36 ml of DMSO. The batch is polymerised and worked up as in Example C2.2.

Yield: 3.81 g (87%), ηinh=0.382 dl/g (0.5% solution in THF at 25° C.), Tg=20.6° C.

D) Preparation of Coating Compositions

EXAMPLE D1

1 mg of the fluoroionophore B3, 1 ml of poly(4-hydroxybutyl acrylate) in 29% isopropanol (catalogue number 888, SPP), 100 μl of 4-hydroxybutyl acrylate (catalogue number M-217, SPP), 50 μl of ethylene glycol diacrylate and azoisobutyronitrile (Fluka, catalogue No. 11630) are mixed in a 2 ml reaction vessel.

EXAMPLE D2

0.35 mg of the fluoroionophore B6, 88 mg of the copolymer from Example C1.3 and 1 ml of isopropanol are mixed in a 2 ml reaction vessel.

E) Manufacture of Sensors

EXAMPLE E1

200 μl of the coating solution from Example D1 are pipetted onto a round microscope cover glass having a diameter of 18 mm and rotated at 700 rpm for 30 seconds using a Convac Spin Coater Model 1001. The coated microscope cover glasses are heated at 60° C. for 3 hours under a nitrogen atmosphere in an oven.

EXAMPLE E2

200 μl of the coating solution from Example D2 are pipetted onto a round microscope cover glass having a diameter of 18 mm and rotated at 500 rpm for 30 seconds using a Convac Spin Coater Model 1001. The coated microscope cover glasses are heated at 60° C. for 3 hours under a nitrogen atmosphere in an oven.

F) Application Examples (Ion Detection)

EXAMPLE F1

The coated microscope cover glasses of Example E1 are fixed in a flow cell. The fluorescence intensity is measured as a function of the concentration of potassium. The measured signals are listed in Table 1.

TABLE 1

| Potassium concentration (millimolar) | Fluorescence intensity (volts) |
|---|---|
| 0 | 6.25 |
| 0.2 | 6.10 |
| 1.0 | 5.93 |
| 2.0 | 5.80 |
| 6.0 | 5.74 |
| 10.0 | 5.70 |
| 14.0 | 5.55 |
| 20.0 | 5.50 |

EXAMPLE F2

The coated microscope cover glasses of Example E2 are fixed in a flow cell. The fluorescence intensity is measured as a function of the concentration of sodium. The measured signals are listed in Table 2.

| Sodium concentration (millimolar) | Fluorescence intensity (volts) |
|---|---|
| 0 | 3.497 |
| 5.0 | 3.522 |
| 25.0 | 3.629 |
| 50.0 | 3.738 |
| 150.0 | 4.064 |
| 250.0 | 4.314 |
| 350.0 | 4.605 |
| 500.0 | 4.887 |

What is claimed is:

1. A compound of formula (I)

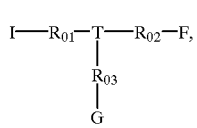

(I)

wherein

I is the monovalent residue of an ionophore,

F is the monovalent residue of a fluorophore,

G is a functional group,

T is a trivalent organic radical and $R_{01}$, $R_{02}$ and $R_{03}$ are each independently of the others a direct bond or a bridging group.

2. A compound according to claim 1 wherein $R_{01}$, $R_{02}$ and $R_{03}$ are each independently of the others a bridging group.

3. A compound according to claim 1 wherein the functional group G is a carboxy or sulfonic acid, carboxy or sulfonic acid halide, carboxy or sulfonic acid amide, carboxy or sulfonic acid ester, thiol, amine, hydroxyl, cyanate, isocyanate, oxime, aldehyde or ketone group, or a polymerisable group.

4. A compound according to claim 3 wherein the polymerisable group is selected from the group —O—$R_8$, —S—$R_8$, —$NR_7R_8$, —$NR_7C(O)R_8$, —$OC(O)R_8$, —$C(O)OR_8$, —$C(O)NR_7R_8$, —CH=N—O—$R_8$ and —NH—C(O)—$NR_7R_8$, wherein $R_7$ is H or $C_1$–$C_4$ alkyl and $R_8$ is an olefinic group having from 1 to 12 carbon atoms, the group being bonded to the trivalent radical T directly or via a bridging group $R_{03}$.

5. A compound according to claim 1 wherein the trivalent radical is $C_1$–$C_{20}$alkanetriyl, which is linear or branched and is interrupted by one or more hetero atoms selected from the group O, S and N.

6. A compound according to claim 3 wherein the trivalent radical is a radical of formula Ib or Ic

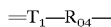 (Ib),

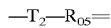 (Ic), wherein $T_1$ is a cycloaliphatic, heterocycloaliphatic, aromatic or heteroaromatic trivalent radical, $T_2$ is a cycloaliphatic, heterocycloaliphatic, aromatic or heteroaromatic divalent radical, $R_{04}$ is a divalent aliphatic radical having from 1 to 20 carbon atoms, and $R_{05}$ is a trivalent aliphatic radical having from 1 to 20 carbon atoms.

7. A compound according to claim 1 wherein the bridging group $R_{01}$ corresponds to formula (IIa)

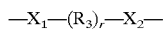 (IIa), the bridging group $R_{02}$ corresponds to formula (IIb)

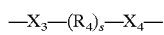 (IIb), and the bridging group $R_{03}$ corresponds to formula (IIc)

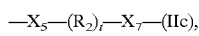 (IIc), wherein $X_1$, $X_2$, $X_3$, $X_4$, $X_5$ and $X_7$ are each independently of the others a direct bond, or $X_1$, $X_2$, $X_3$, $X_4$, $X_5$ and $X_7$ are each independently of the others selected from the group —O—, —S—, —$NR_5$—, —C(O)—O—, —O—C(O)—, —O—C(O)—O—, —$SO_2$—O—, —O—$SO_2$—, —O—$SO_2$—O, —$NR_5$—C(O)—, —C(O)—$NR_5$—, —$NR_5$—C(O)—O—, —O—C(O)—$NR_5$—, —$NR_5$—C(O)—$NR_5$—, —$NR_5SO_2$—, —$SO_2$—$NR_5$—, —$NR_5$—$SO_2$—O—, —O—$SO_2NR_5$— and —$NR_5SO_2$—$NR_5$—, $R_5$ is H or $C_1$–$C_{30}$alkyl, $C_5$- or $C_8$-cycloalkyl, $C_5$- or $C_6$-cycloalkyl-methyl or -ethyl, phenyl, benzyl or 1-phenyleth-2-yl, $R_2$, $R_3$ and $R_4$ are each independently of the others a divalent bridging group, r, s and t are each independently of the others 0 or 1, with the proviso that r, s or t is 1 when $X_1$ or $X_3$ or $X_5$ is one of the said groups.

8. A compound according to claim 1 wherein the ionophore is derived from a 1,3-alternating calix[4]crown-5.

9. A compound according to claim 1 wherein the ionophore is derived from a 1,3-alternating calix[4]crown-5 of formula IV

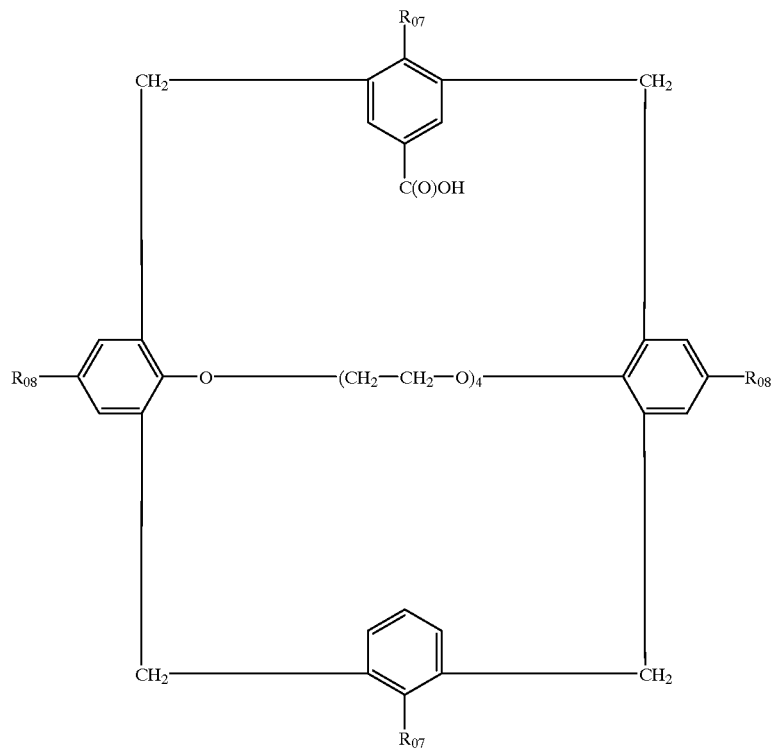

(IV)

wherein $R_{07}$ and $R_{08}$ are each independently of the other H, linear or branched $C_1$–$C_{20}$alkyl, or linear or branched $C_1$–$C_{20}$alkoxy, or an acid derivative thereof.

10. A compound according to claim 1 wherein the ionophore is derived from a calix[4]arene.

11. A compound according to claim 10 wherein the ionophore is derived from a calix[4]arene of formula (IVa)

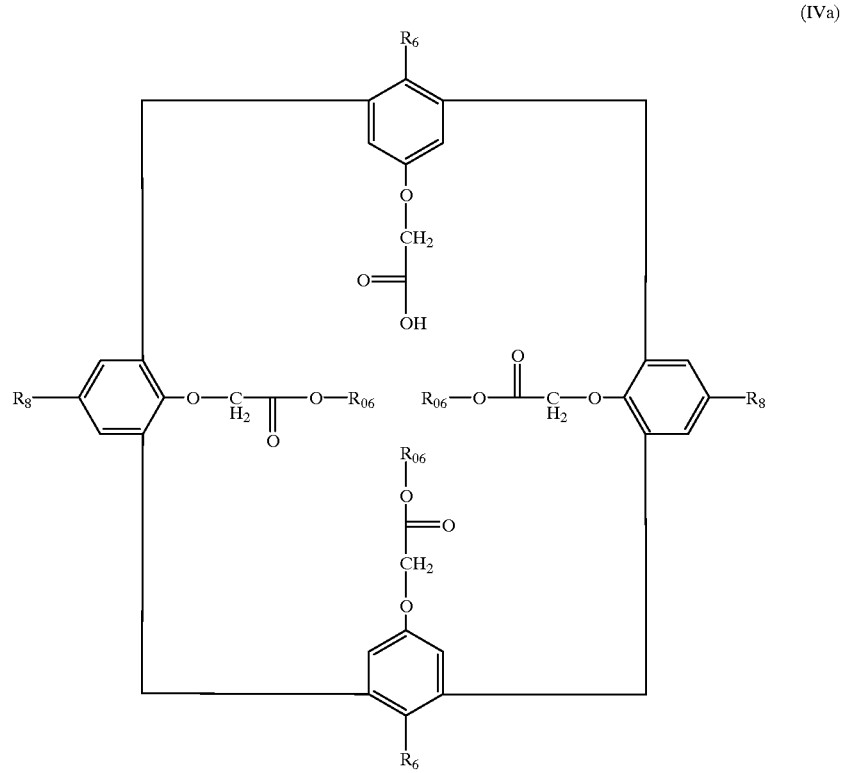
wherein
$R_{06}$ is H or unsubstituted $C_1$–$C_{20}$alkyl, and
$R_6$ is H or unsubstituted $C_1$–$C_{30}$alkyl.
12. A compound according to claim 1 wherein the fluorophore from which F in formula (I) is derived is a compound of one of the formulae A–F
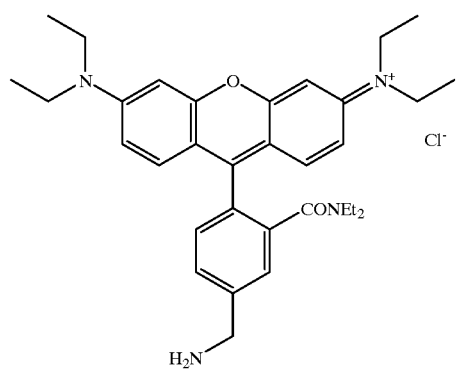
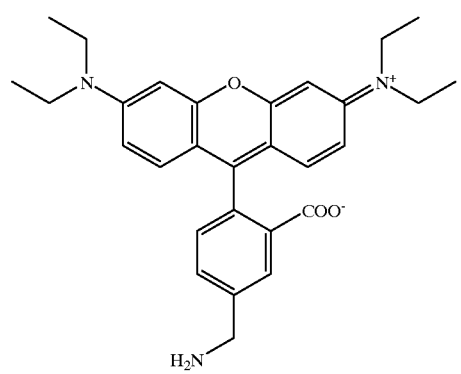
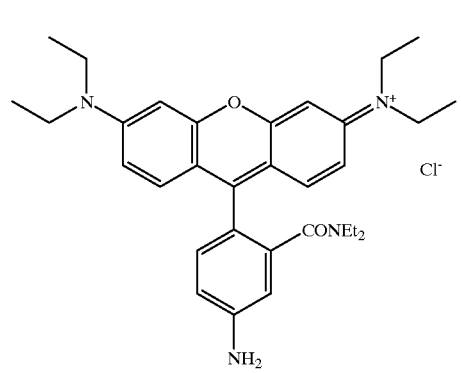

-continued

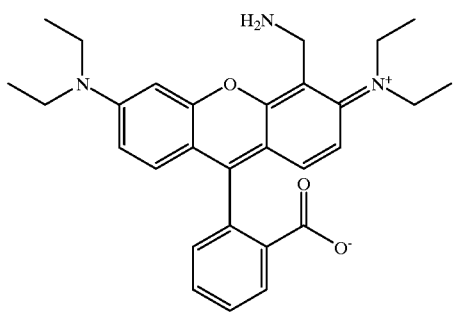

D

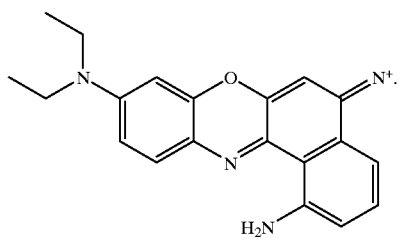

F

13. A compound according to claim 1 wherein the fluorophore from which F in formula (I) is derived is an acridine of formula

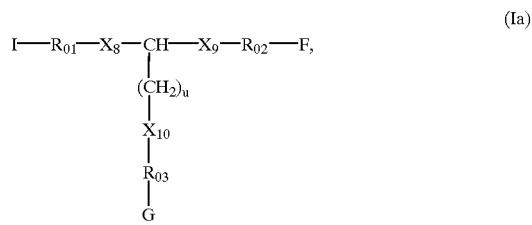

or a derivate thereof wherein $R_{01}$ and $R_{02}$ are each independently of the other H or $C_1$–$C_{20}$alkyl and $R_{03}$ is H or $C_1$–$C_6$alkyl.

14. A compound according to claim 1 which is a fluoroionophore of formula (Ia)

$$I\text{---}R_{01}\text{---}X_8\text{---}\underset{\underset{\underset{G}{R_{03}}}{\underset{X_{10}}{(CH_2)_u}}}{CH}\text{---}X_9\text{---}R_{02}\text{---}F, \qquad (Ia)$$

wherein $X_8$, $X_9$ and $X_{10}$ are each independently of the others —C(O)O—, —OC(O)—, —C(O)NR$_5$— or —NR$_5$—C(O)—, and I, $R_{01}$, $R_{02}$, $R_{03}$, G and F are as defined in claim 1, u is an integer from 1 to 6, and the $R_5$ radicals are each independently of the other H or $C_1$–$C_4$alkyl.

15. A compound according to claim 1 which is a fluoroionophore of the formula

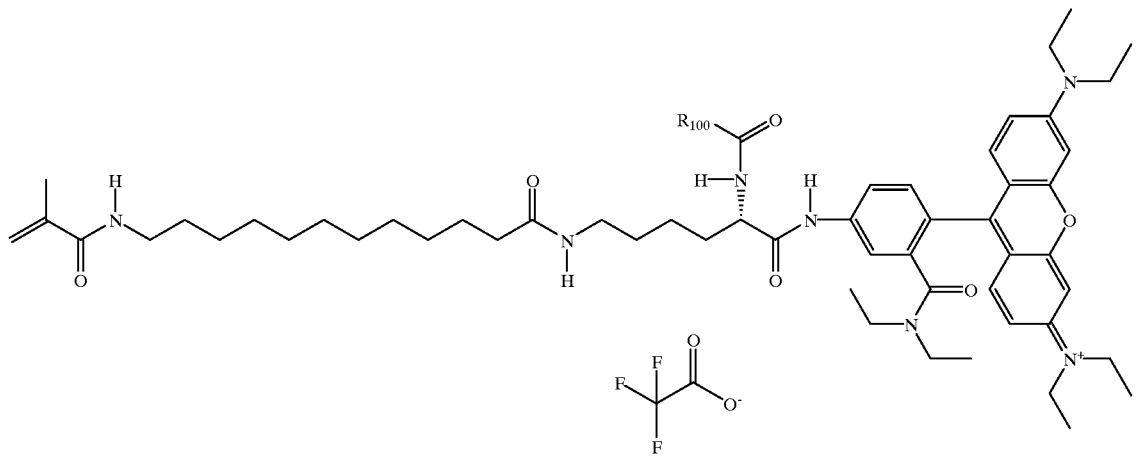

wherein $R_{100}$ is a residue of formula
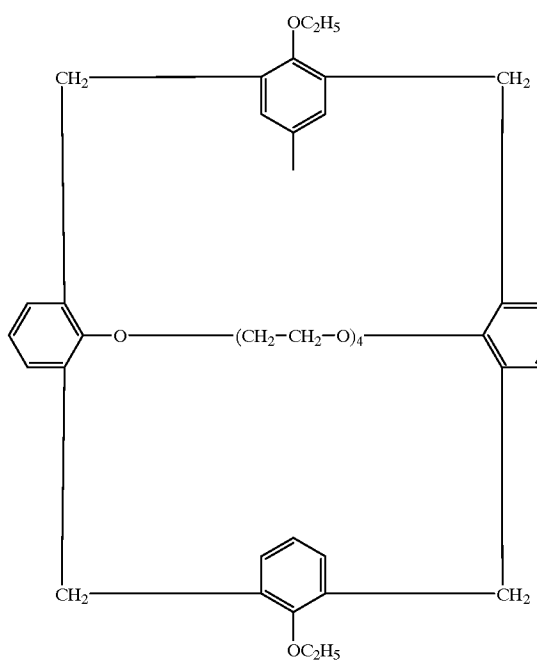
16. A compound according to claim 1 which is a fluoroionophore of the formula
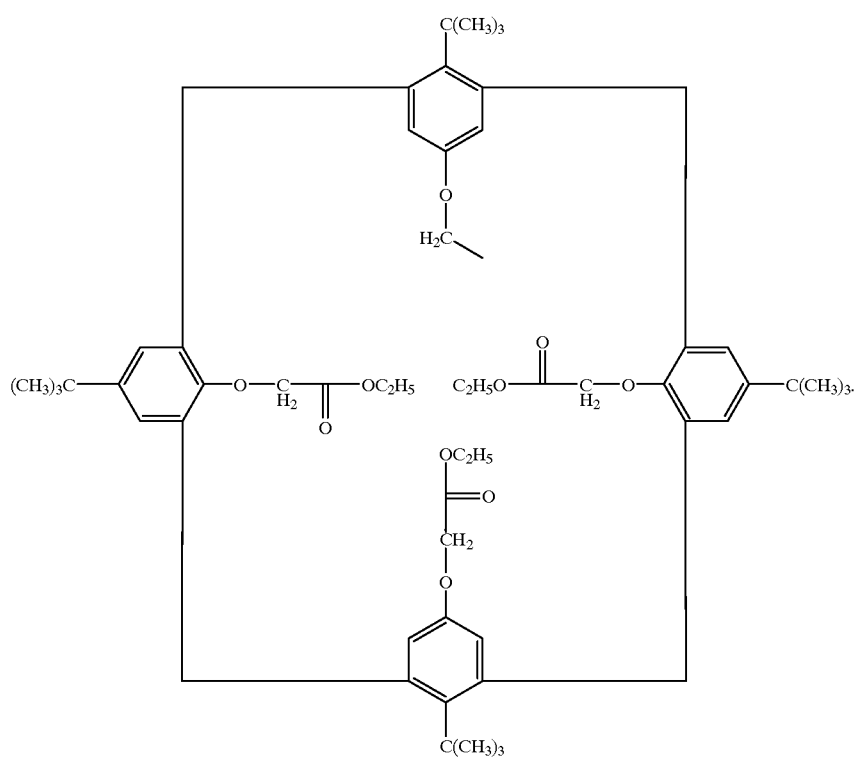
17. A compound according to claim 1 which is a fluoroionophore of the formula
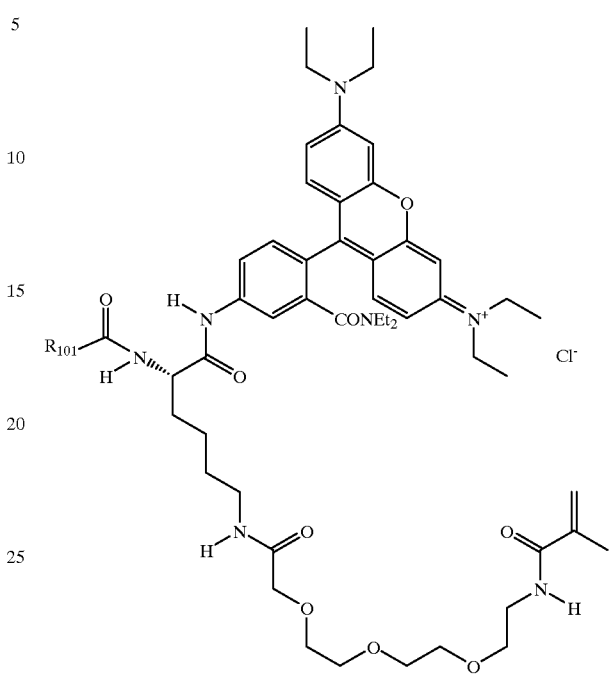

wherein $R_{101}$ is a residue of formula

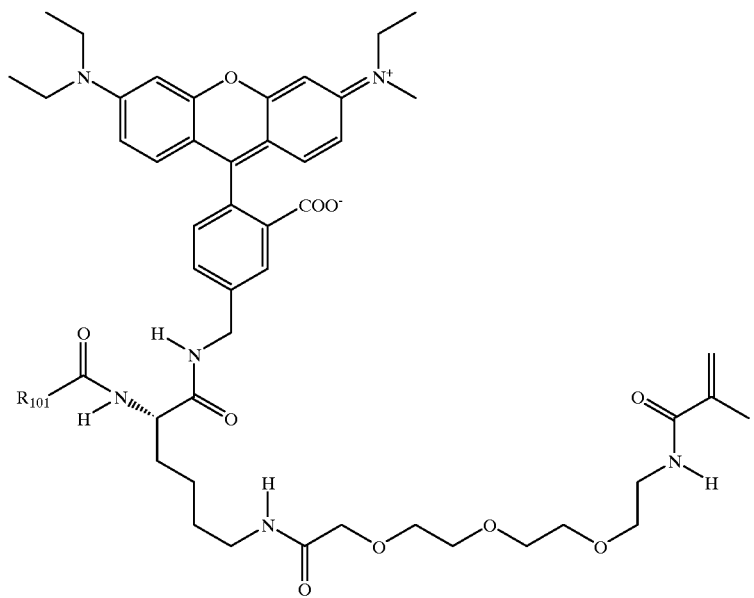

wherein $R_{101}$ is a residue of formula

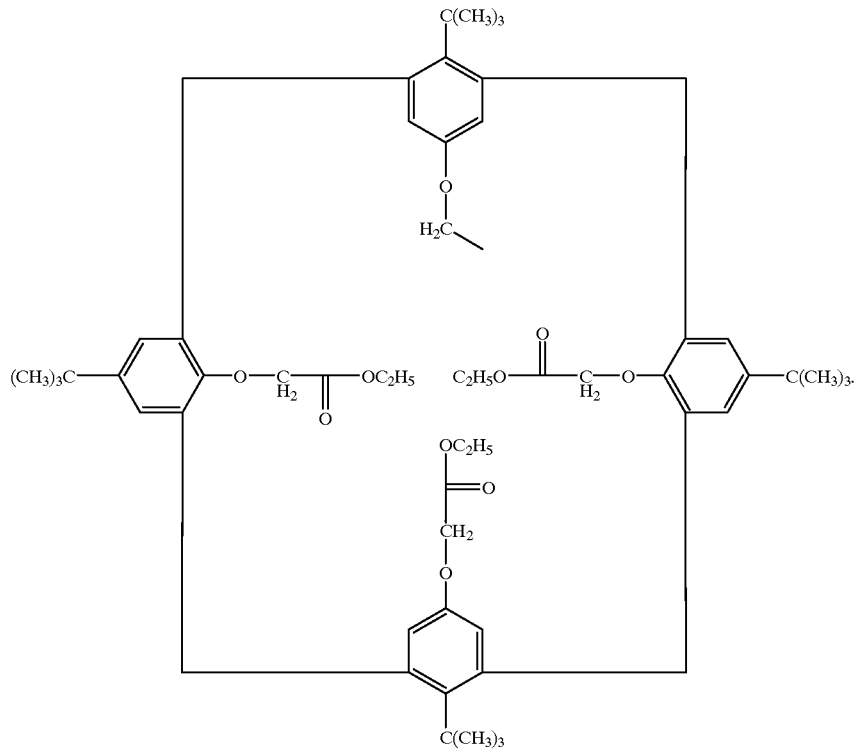

18. A composition comprising (a) an inorganic or organic carrier material to which (b) a fluoroionophore of formula (I) as claimed in claim 1 is bonded via the functional group G directly or via a bridging group.

19. A composition according to claim 18 wherein the carrier material is an organic carrier material which is a polymer comprising monomers having covalently bound fluoroionophore.

20. A composition according to claim 18 wherein the carrier material is a finely divided inorganic or organic carrier material to the surface of which the fluoroionophore is covalently bound.

21. A composition according to claim 19 wherein the amount of fluoroionophore covalently bound to the carrier material is from 0.0001 to 99% by weight based on the carrier material.

22. A material comprising (a) a support and (b) an active layer on at least one surface, wherein the active layer consists (1) of a polymer comprising monomers having covalently bound a fluoroionophore of formula I as claimed in claim 1, alone or in admixture with a natural or synthetic polymer, or (2) of a natural or synthetic polymer in which particles of a finely divided inorganic or organic carrier material to the surface of which a fluoroionophore of formula I as claimed in claim 1 is covalently bound are incorporated.

23. A composition comprising (a) a compound of formula I as claimed in claim 1 alone or (b) together with at least one comonomer and, where appropriate, a solvent for components (a) and (b).

24. A method for the optical determination of ions in aqueous test samples, in which an active layer of the material according to claim 22 is brought into contact with an aqueous test sample and then a change in fluorescence is measured.

25. A method for the determination of ions in an aqueous test sample, wherein an optical sensor comprising (a) an inorganic or organic carrier material to which (b) a fluoroionophore of formula I as claimed in claim 1 is bonded via the functional group G directly or via a bridging group is brought into contact with said aqueous test sample and then a change in fluorescence of the fluorophore is measured.

26. An optical sensor for the determination of cations or anions by spectroscopy, comprising a material according to claim 22.

* * * * *